(12) United States Patent
Nakamura et al.

(10) Patent No.: US 6,184,352 B1
(45) Date of Patent: Feb. 6, 2001

(54) ADSEVERIN PROTEIN

(75) Inventors: Seiji Nakamura, deceased, late of Chiba-ken, by Noriko Nakamura, heir; Takashi Sakurai; Juni-ichi Nezu, both of Tokyo, all of (JP)

(73) Assignee: Chugai Seiyaku Kabushiki Kaisha, Tokyo (JP)

( * ) Notice: Under 35 U.S.C. 154(b), the term of this patent shall be extended for 0 days.

(21) Appl. No.: 09/469,253

(22) Filed: Dec. 22, 1999

Related U.S. Application Data

(62) Division of application No. 08/669,286, filed as application No. PCT/JP94/02227 on Dec. 27, 1994.

(30) Foreign Application Priority Data

Dec. 28, 1993 (JP) ................................. 5-355112
Jul. 12, 1994 (JP) ................................. 6-160236
Dec. 20, 1994 (JP) ................................. 6-340692

(51) Int. Cl.$^7$ ................................................ C07K 14/00
(52) U.S. Cl. ............................................................ 530/350
(58) Field of Search ........................ 435/69.1, 70.1, 435/320.1, 325; 530/350

(56) References Cited

FOREIGN PATENT DOCUMENTS

WO9115770   10/1991  (WO) .

OTHER PUBLICATIONS

Sakurai et al., The Ca2 + –dependent actin filament–severing activity of 74–kDa protein protein (adseverin) resides in its NH2–terminal half, JBC, vol. 266 (7), pp. 4581–4585, Mar. 1991.*

Sakurai et al., Comparison between the gelsolin and adseverin domain structure, JBC, vol. 266, (24), pp. 15979–15983, Aug. 1991.*

Del Castillo et al., Chromaffin cell scinderin, a novel calcium dependent actin filament–severing protein, EMBO, vol. 9 (1), pp. 43–52, 1990.*

Database EMBL, Entry MM04354, Accession No. U04354, Dec. 17, 1993.

A. Rodriguez, et al. , *The EMBO Journal*, vol. 9, No. 1, pp. 43–52, (1990).

L. Tchakarov, et al., *FEBS Letters*, vol. 268, No. 1, pp. 209–212 (1990).

M. G. Marcu, et al. *Molecular and Cellular Biochemistry*, vol. 141, No. 2, pp. 153–165, (1994).

P. A. Janmey, et al., *Blood*, vol. 80, No. 4, pp. 928–936, (1992).

Berendsen. *Science*, vol. 282, pp. 642–643, (Oct. 1998).

S. Nakamura, et al. *J. of Biological Chemistry*, vol. 8, No. 269, pp. 5890–5896, (1994).

S. Nakamura, et al. *Jpn. J. Pharmacol.*, vol. 61, Suppl.1, p. 294, (1993).

T. Sakurai, et al. *J. of Biological Chemistry*, vol. 266, No. 24, pp. 15979–15983, (1991).

T. Sakurai, et al. *Journal of Biological Chemistry*, vol. 266, No. 7, pp. 4581–4585, (1991).

T. Sakurai, et al. *Neuroscience*, vol. 38, No. 3, pp. 743–756, (1990).

* cited by examiner

*Primary Examiner*—Robert A. Schwartzman
*Assistant Examiner*—Andrew Wang
(74) *Attorney, Agent, or Firm*—Birch, Stewart, Kolasch & Birch, LLP

(57) ABSTRACT

A DNA containing a base sequence encoding an amino acid sequence represented by SEQ ID NO: 4 or 6 in Sequence Listing, which optionally has partial replacement, deletion or addition, or a base sequence hybridizable therewith; a recombinant vector containing this gene; a transformant constructed by using this vector; a process for producing adseverin by using the above-mentioned gene; a recombinant adseverin protein obtained by this production process; an oligonucleotide hybridizable specifically with a base sequence encoding an amino acid sequence represented by SEQ ID NO: 4 or 6; a method for regulating the formation of adseverin in an animal which comprises administering the above-mentioned oligonucleotide to the animal; and an antibody capable of recognizing adseverin protein.

2 Claims, 13 Drawing Sheets

```
adseverin C39      K V A H V K Q I P F D A
gelsolin       386 H I A N V E R V P F D A
villin         365 K V A K V E Q V K F D A
```

Fig. 5A

```
ADS 008  EEFAR-AGK-R  AGLQVWRIE  KLELVPVPESAYGN
GEL 057  PEFLK-AGK-E  PGLQIWRVE  KFDLVPVPTNLYGD    1
VIL 007  QVKGS-LNITT  PGLQIWRIE  AMQMVPVPSSTFGS

ADS 385  AAQHHVVDDGS  GKVQIWRVE  NNGRVEIDRNSYGE
GEL 434  AAQHGMDDDGT  GQKQIWRIE  GSNKVPVDPATYGQ    4
VIL 387  AAQQKMVDDGS  GEVQVWRIE  NLELVPVDSKWLGH

ADS 127  NHVLTNDLTAQ  RLLHVKGRR  -VVRATEVPLSWDS
GEL 177  KHVVPNEVVVQ  RLFQVKGRR  -VVRATEVPVSWES    2
VIL 127  KHVETNSYDVQ  RLLHVKGKR  NVV-AGEVEMSWKS

ADS 503  GQAPAPPI--RL  FQVRRNLAS  ITRIM-EVDVDANS
GEL 556  GQTAPAST--RL  FQVRANSAG  ATRAV-EVLPKAGA    5
VIL 508  NLETGPST--RL  FQVQGTGAN  NTKAF-EVPARANF

ADS 245  NRKMAK-LYMV  SDASGSMKV  SLVAEENPFSMAM
GEL 294  NRKLAK-LYKV  SNGAGTMSV  SLVADENPFAQGA    3
VIL 250  KAAL-K-LYHV  SDSEGNLVV  REVAT-RPLTQDL

ADS 610  ED-HPPRLYGC  SNKTGRFII  EEVPGE--FTQDD
GEL 662  MDAHPPRLFAC  SNKIGRFVI  EEVPGE--LMQED    6
VIL 615  LVI-TPRLFEC  SNKTGRFLA  TEIP-D--FNQDD
```

Fig. 5D

```
ADS  -  -KGGLKY----KA  GGVASGL     126  1
GEL  -  -KSGLKY----KK  GGVASGF     176
VIL  -  -KQGLVI----RK  GGVASGM     126

ADS  -  ---KDKPLIIY  KNGTSKKE      502  4
GEL  -  ---GGKPMIIY  KGGTSREG      555
VIL  -  ---KGR-MVVY  QGGTSRTN      507

ADS  -  ---GEKPKLRD  GEDDDIKADIT   244  2
GEL  -  ---GPKPALPA  GTEDTA-KEDAA  293
VIL  N  HVLGKRRELKA  AVPDTV-VEPAL  249

ADS  -  ---GGK---KD  YQTS-PLLESQA  609  5
GEL  -  ---GGK---AA  YRTS-PRLKDKK  661
VIL  -  ---GGK---AP  YANT-KRLQEEN  614

ADS  K  DWRDRDQSDGF  GKVYVTEKVAH   367  3
GEL  K  NWRDPDQTDGL  GLSYLSSHIAN   416
VIL  Q  KWTASNRTSGL  GKTHTVGSVAK   369

ADS  G  WDSSRW                     715  6
GEL  G  WDDDYWSVDPL  -DRAMAELAA    782
VIL  A  WDPFKWSNTKS  YEDLKAESGN    734
```

```
  1' MARELYHEEFARAGKQAGLQVWRIEKLELVPVPQSAHGDFYVGDAYLVLHTAKTSRGFTY
     **  **********  ************   **  *  ************    ******
  1" MAQGLYHEEFARAGKRAGLQVWRIEKLELVPVPESAYGNFYVGDAYLVLHTTQASRGFTY

61' HLHFWLGKECSQDESTAAAIFTVQMDDYLGGKPVQNRELQGYESNDFVSYFKGGLKYKAG
     *********** ********************************* *** * *********
 61" RLHFWLGKECTQDESTAAAIFTVQMDDYLGGKPVQNRELQGYESTDFVGYFKGGLKYKAG

121' GVASGLNHVLTNDLTAKRLLHVKGRRVVRATEVPLSWDSFNKGDCFIIDLGTEIYQWCGS
     ****************  *****************************************
121" GVASGLNHVLTNDLTACRLLHVKGRRVVRATEVPLSWDSFNKGDCFIIDLGTEIYQWCGS

181' SCNKYERLKANQVATGIRYNERKGRSELIVVEEGSEPSELIKVLGEKPELPDGGDDDDII
     ********** ***  ***  *******  ************** *  *  *  *****
181" SCNKYERLKASQVAIGIRDNERKGRAQLIVVEEGSEPSELTKVLGEKPKLRDGEDDDDIK

241' ADISNRKMAKLYMVSDASGSMRVTVVAEENPFSMAMLLSEECFILDHGAAKQIFVWKGKD
     ***  *************** *   *  ******************************
241" ADITNRKMAKLYMVSDASGSMKVSLVAEENPFSMAMLLSEECFILDHGAAKQIFVWKGKD

301' ANPQERKAAMKTAEEFLQQMNYSKNTQIQVLPEGGETPIFKQFFKDWRDKDQSDGFGKVY
     **********************  ********************** ** **********
301" ANPQERKAAMKTAEEFLQQMNYSTNTQIQVLPEGGETPIFKQFFKDWRDRDQSDGFGKVY

361' VTEKVAQIKQIPFDASKLHSSPQMAAQHNMVDDGSGKVEIWRVENNGRIQVDQNSYGEFY
     ******  * ********************** ********* ********** *****
361" VTEKVAHVKQIPFDASKLHSSPQMAAQHHVVDDGSGKVQIWRVENNGRVEIDRNSYGEFY

421' GGDCYIILYTYPRGQIIYTWQGANATRDELTTSAFLTVQLDRSLGGQAVQIRVSQGKEPV
     ***********************************************************
421" GGDCYIILYTYPRGQIIYTWQGANATRDELTTSAFLTVQLDRSLGGQAVQIRVSQGKEPA

481' HLLSLFKDKPLIIYKNGTSKKGGQAPAPPTRLFQVRRNLASITRIVEVDVDANSLNSNDV
     ****************** *** ****** ************** ***************
481" HLLSLFKDKPLIIYKNGTSKKEGQAPAPPIRLFQVRRNLASITRIMEVDVDANSLNSNDV

541' CVLKLPQNSGYIWVGKGASQEEEKGAEYVASVLKCKTLRIQEGEEPEEFWNSLGGKKDYQ
     ****  *****  ***  ****************** ** *****************
541" FVLKLRQNNGYIWIGKGSTQEEEKGAEYVASVLKCKTSTIQEGKEPEEFWNSLGGKKDYQ

601' TSPLLETQAEDHPPRLYGCSNKTGRFVIEEIPGEFTQDDLAEDDVMLLDAWEQIFIWIGK
     ******  ************** ***   ***********************************
601" TSPLLESQAEDHPPRLYGCSNKTGRFIIEEVPGEFTQDDLAEDDVMLLDAWEQIFIWIGK

661' DANEVEKKESLKSAKMYLETDPSGRDKRTPIVIIKQGHEPPTFTGWFLGWDSSKW
     ******* ******* ******************************************
661" DANEVEKSESLKSAKIYLETDPSGRDKRTPIVIIKQGHEPPTFTGWFLGWDSSRW
```

ADSEVERIN PROTEIN

This application is a divisional of co-pending application Ser. No. 08/669,286, filed on Jun. 28, 1996. Application Ser. No. 08/669,286 is the national phase of PCT International application Ser. No. PCT/JP94/02227 filed on Dec. 27, 1994 under 35 U.S.C. § 371. The entire contents of each of the above-identified applications are hereby incorporated by reference.

TECHNICAL FIELD

This invention relates to a gene encoding adseverin, which is a $Ca^{2-}$-dependent actin filament-severing protein and has a function of regulating exocytosis, a recombinant vector containing this gene, a recombinant transformed by this vector, a process for producing adseverin by using the above-mentioned gene and a recombinant adseverin protein obtained by this process. The present invention also relates to an oligonucleotide hybridizable specifically with a base sequence encoding the adseverin protein, a method for regulating the formation of adseverin which comprises administering an oligonucleotide hybridizable specifically with a base sequence encoding the adseverin protein to an animal, and an antibody capable of recognizing the adseverin protein.

BACKGROUND ART

In many secretory cells in the resting state, secretion products such as neurotransmitters and hormones are stored in the form of granules or vesicles. When the cells receive adequate signals, these substances are released from the cells by exocytosis. In the process of exocytosis, the granules and vesicles migrate toward plasma membrane. Then they come into contact with the plasma membrane followed by fusion therewith, thus opening the membrane.

This exocytosis is tightly controlled by the concentration of intracellular free calcium $[Ca^{2+}]_i$ (Knight et al., Ann. N.Y. Acad. Sci. 493:504–523, 1987). Namely, it is considered that in resting cells where $[Ca^{2+}]_i$ is low, exocytosis is blocked at several steps depending on $[Ca^{2+}]_i$ (Burgoyne, Biochem. Biophys. Acta 779:201–216, 1984). A number of secretory cells including chromaffin cells which are adrenal medulla secretory cells have a microfilament network composed of actin filaments under the plasma membrane which is supposed to serve as a barrier against the migration of granules and vesicles toward the plasma membrane (Cheek et al., FEBS Lett. 207:110–114, 1986; Lelkes et al., FBES Lett. 208:357–363, 1986). Prior to the release of the secretion products by exocytosis, this network is disassembled due to the increase in $[Ca^{2+}]_i$ by $Ca^{2+}$-dependent mechanisms (Vitale et al., J. Cell Biol. 113:1057–1067, 1991).

Actin is a globular protein with a molecular weight of 42 kD which is commonly distributed in eukaryocytes. It is a cytoskeleton protein closely relating to the contraction of muscle cells, etc. Actin membranes are polymerized to form filaments. Under the physiological ionic strength, actin undergoes polymerization in vitro at a ratio of about 100% so as to give filaments. In actual cells, however, various actin-regulating proteins contribute to the reversible conversion of filaments (gel) and monomers (sol) and changes occur depending on extracellular stimuli.

In bovine chromaffin cells, gelsolin, which seemingly relates directly to this process, was identified (Yin et al., Nature 281:583–586, 1979). Gelsolin shows a $Ca^{2+}$-dependent actin filament severing activity in vitro and exerts barbed end capping and nucleating activities on actin filaments. Recently, adseverin (a protein of 74 kDa), which is similar to gelsolin in activity but different from it, was isolated from bovine adrenal medulla by Prof. Nonomura et al., Department of Pharmacology, Faculty of Medicine, University of Tokyo (Maekawa et al., J. Biol. Chem. 265:10940–10942).

Gelsolin is relatively widely distributed in various tissues and blood plasma (Stossel et al., Annu. Rev. Cell Biol. 1:353–402, 1985), while the distribution of adseverin is restricted mainly to the tissues with secretory functions (Sakurai et al., Neuroscience 38:743–756, 1990). This difference in tissue distribution of these proteins suggests that adseverin more closely relates to the secretory process (i.e., control of the release of neurotransmitters, endocrine substances or physiologically active substances) than gelsolin does. Accordingly, it is highly interesting to reveal the structure and function of adseverin to thereby clarify the role and regulatory mechanisms of actin filaments in exocytosis.

In former days, it was generally regarded that this process was regulated by fused proteins, etc. [Nishizaki, "Kaiko Hoshutsu Gesho ni okeru Saiboshitsu Tanpakushitsu no Yakuwari (Roles of Cytoplasmic Proteins in Exocytosis)", Saibo Kogaku (Cell Technology), 13:353–360, 1994]. However, Nonomura et al. newly point out in their hypothesis that this process finally depends on an interaction between actin and myosin. This hypothesis further provides an epoch-making idea that the regulation by the actin-severing protein takes place in non-muscular cells on the actin side, differing from the regulation on the myosin side by myosin light chain kinase [Mochida, "Miosin Keisa Kinaze Shinkei Dentatsu Busshitsu Hoshutsu to sono Chosetsu ni okeru Miosin Keisa Kinaze no Yakuwari (Role of Myosin Light Chain Kinase in Release of Myosin Light Chain Kinase Neutrotransmitter and Regulation thereof)", Saibo Kogaku (Cell Technology), 13:381–388, 1994].

It is thought that actin is liberated from broken cells and induces or enhances platelet agglutination in the blood so as to trigger thrombus development (Scarborough et al., Biochem. Biophys. Res. Commun. 100:1314–1319, 1981). On the other hand, adseverin has a gelsolin-like activity (i.e., an actin filament-severing activity) in vivo as described above. These facts indicate that adseverin might be applicable to drugs relating to thrombus (for example, thrombosis inhibitors).

It is furthermore expected that the release of, for example, a physiologically active substance might be regulated at the gene level by administering the antisense DNA sequence constructed on the basis of the base sequence encoding adseverin. Since adseverin might closely relate to the multiplication of vascular smooth muscles, it is considered that the administration of the antisense DNA would regulate the function of adseverin to thereby inhibit the multiplication of the smooth muscles. Accordingly, it is expected that the administration of the antisense DNA of adseverin might be usable in the inhibition of angiostenosis in blood vessel transplantation in bypass operation, etc. or in the inhibition of restenosis after percutaneous transluminal coronary angioplasty (PTCA).

To use the actin-regulating protein adseverin in the medicinal purposes as described above, it is necessary to produce adseverin in a large amount and in a uniform state. However, it is difficult to obtain uniform adseverin in a large amount by the conventional method wherein adseverin is isolated from an animal tissue per se or the culture supernatant of adseverin-producing cells. It is therefore required to clarify the base sequence of the gene encoding adseverin so as to produce adseverin in a large amount by using gene recombination techniques.

An object of the present invention is to identify the base sequence of the gene encoding adseverin. Another object of the present invention is to produce adseverin in a large amount by using gene recombination techniques with the use of a recombinant vector containing the above-mentioned sequence and the construct a screening system, etc. by using the same, thus developing novel drugs. Another object of the present invention is to produce the antisense DNA on the basis of the base sequence of the gene encoding adseverin and use it as a drug for inhibiting the formation of adseverin. Another object of the present invention is to provide an antibody capable of recognizing the adseverin protein.

The present inventors isolated and purified adseverin from bovine adrenal medulla and clarified its properties (Sakurai et al., Neuroscience 38:743–756, 1990; Sakurai et al., J. Biol. Chem. 226;4581–4584, 1991; Sakurai et al., J. Bio. Chem. 266:15979–15983, 1991).

Further, a hydrolyzed fragment of this protein was obtained and, based on the partial information of its amino acid sequence, oligonucleotide primers were synthesized. On the other hand, cDNA was prepared by reverse transcription from mRNA prepared from MDBK cells, a cell line established from bovine kidney (JCRB-Cell, obtained from Japan Foundation for Cancer Research). Then polymerase chain reaction (PCR) was performed with the use of the primers synthesized above to thereby specifically amplify the DNA fragment encoding bovine adseverin. Next, a cDNA library prepared from bovine adrenal medulla was screened by using the above-mentioned DNA fragment labeled with $^{32}$P as a probe. From 3 overlapping clones thus obtained, the target gene encoding the actin filament-severing protein was assembled. Thus the entire base sequence of the gene was successfully identified.

Subsequently, the present inventors employed this bovine adseverin cDNA as a probe and screened a cDNA library prepared from human kidney mRNA by plaque hybridization under less stringent conditions. Thus they isolated human adseverin cDNA and successfully identified the entire base sequence of the same.

DISCLOSURE OF THE INVENTION

The present invention provides a gene encoding adseverin. More particularly, it provides a DNA containing a base sequence encoding the amino acid sequence represented by SEQ ID NO: 4 or SEQ ID NO: 6 in Sequence Listing, which optionally has partial replacement, deletion or addition, or a base sequence hybridizable therewith.

The present invention further provides a recombinant vector containing the gene encoding the adseverin protein.

The present invention furthermore provides prokaryotic or eukaryotic host cells transformed by the recombinant vector containing the gene encoding the adseverin protein.

The present invention furthermore provides a process for producing human adseverin protein which comprises incubating a transformant, which has been obtained via transformation by the recombinant vector containing the gene encoding the adseverin protein, and isolating and purifying the target protein thus produced.

The present invention furthermore provides the recombinant adseverin protein produced by the above-mentioned process.

The present invention furthermore provides an oligonucleotide hybridizable specifically with the gene encoding adseverin.

The present invention furthermore provides a method for regulating the formation of adseverin in an animal which comprises administering an oligonucleotide hybridizable specifically with the gene encoding adseverin to the animal.

The present invention furthermore provides an antibody capable of recognizing the adseverin protein.

By using a labeled adseverin cDNA fragment as a probe, the present inventors further performed in situ hybridization and studied the expression of adseverin mRNA in tissues to thereby clarify the distribution of adseverin in the tissues. Also, the actin-severing domain in adseverin was examined.

BRIEF DESCRIPTION OF THE DRAWINGS

FIGS. 5A–5E show the amino acid sequence of bovine adseverin, which has been identified in the present invention (SEQ ID NO: 5), in comparison with the amino acid sequences of the corresponding segments of human gelsolin (SEQ ID NO: 10) and human villin (SEQ ID NO: 11). The numbers at the right side designate the segment numbers for adseverin, gelsolin and villin. The largest homology resides between the segments 1 and 4, 2 and 5 and 3 and 6. The highly conserved motif sequences are shown in boxes. Putative polyphosphoinositide binding sites are boxed by dotted lines. The diagram with ellipses numbered 1 to 6 given below indicates 6 homologous segments of these proteins.

FIG. 6A shows SDS-PAGE analysis of the expression of adseverin in *E. coli*. The transformant was incubated in the presence (lane 3) or absence (lane 2) of 0.4 mM IPTG for 3 hours. Then the pelleted cells were dissolved in an SDS sample buffer, heated and loaded onto an SDS-polyacrylamide gel. After electrophoresing, the gel was stained with Coomassie brilliant blue. The arrow indicates the adseverin band. Lane 1 shows molecular weight markers. FIG. 6B shows immunoblot analysis performed after the expression of adseverin in E. coli and purification of the same. The purified adseverin was separated with SDS-PAGE and transferred onto a nitrocellulose membrane. The blot was stained with Ponceau S (lane 2) and, after destaining, immunodetected with the use of an affinity purified antibody against adseverin (lane 3). Lane 1 shows molecular weight markers.

FIGS. 7A–7B show the effects of adseverin expressed in E. coli on actin polymerization measured with a viscometer. Actin was polymerized in buffer P containing 0.1 mM of $CaCl_2$ (7A) or 1 mM of EGTA (7B).

FIG. 9 shows a comparison between the amino acid sequence of human adseverin and the amino acid sequence of bovine adseverin. In FIG. 9, the upper and lower columns correspond respectively to the human amino acid sequence (SEQ ID NO: 7) and the bovine amino acid sequence (SEQ ID NO: 5). These amino acid sequences are completely identical with each other at the amino acids with the mark * and highly analogous at the amino acids with the mark. Putative phospholipid binding sites are boxed by solid lines.

Figure 1:
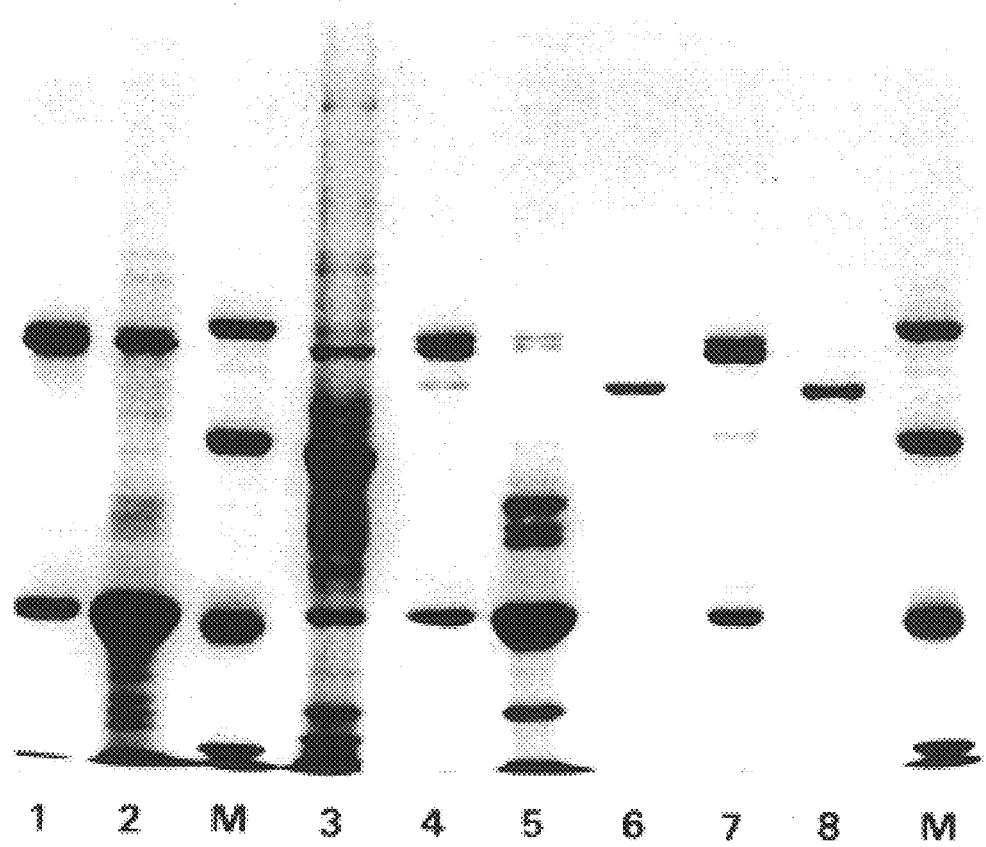
FIG. 1 is a photograph which shows the electrophoretic pattern of purified adseverin obtained from bovine adrenal medulla in comparison with purified gelsolin obtained from bovine aorta. SDS-PAGE was carried out by using 6.5–10.5% linear gradient gel. Lanes 1 and 2 show fractions from bovine aorta treated with a DNase I affinity column. Lane 1 corresponds to the EGTA eluate, while lane 2 corresponds to the 6 M urea eluate. Lanes 3 to 8 show fractions obtained from bovine adrenal medulla. Namely, lanes 3, 4, 5, 6, 7 and 8 correspond respectively to: the crude extract; the EGTA eluate of the DNase I affinity column; the 6 M urea eluate of the DNase I affinity column; the Q-Sepharose fraction containing adseverin; the Q-Sepharose fraction containing plasma gelsolin, cytoplasmic gelsolin and actin; and adseverin purified by HPLC gel filtration. Lane M shows molecular weight markers of 94,000, 67,000, 43,000 and 30,000 from top to bottom.

DETAILED DESCRIPTION OF THE INVENTION cDNA encoding adseverin can be obtained by, for example, preparing mRNA from adseverin-producing cells and then converting it into a double stranded cDNA by a known method.

In the present invention, mRNA of the bovine adseverin are obtained from MDBK cells, which is a cell line established from bovine kidney, and bovine adrenal medulla (Madin et al., Proc. Soc. Exp. Biol. 98:574–576, 1958), while mRNA of the human adseverin is obtained from human kidney mRNA purchased from CLONTECH Laboratories Inc. However the mRNA sources are not restricted thereto but use can be made of adrenal medulla chromaffin cells, kidney medulla, thyroid tissue homogenizate, etc. therefor.

The RNA may be prepared in accordance with, for example, the method of Chirgwin et al. (Biochemistry 18:5294–5299, 1979). Namely, the whole RNA can be obtained by treating the RNA source with guanidine thiocyanate followed by cesium chloride gradient centrifugation. Alternatively, use can be also made of methods employed for cloning genes of other physiologically active proteins, for example, treatment with a surfactant or phenol in the presence of a ribonuclease inhibitor (for example, a vanadium complex).

To obtain the double stranded cDNA from the mRNA thus obtained, reverse transcription is performed by, for example, using the mRNA as a template and an oligo (dT) or random primer, which is complementary to the poly A-chain at the 3'-end, or an synthetic oligonucleotide, which corresponds to a part of the amino acid sequence of adseverin, as a primer so as to synthesize a DNA (cDNA) complementary to the mRNA.

In the present invention, the bovine adseverin cDNA is obtained in the following manner. Namely, reverse transcription is carried out by using random hexamers as primers. Next, the resulting product is amplified by PCR with the use of condensed primers to give a PCR product corresponding to a partial cDNA of adseverin of about 700 bp. Then this PCR product is subcloned into pBluescript SK(-) (Stratagene). Next, A λgt11 cDNA library prepared from bovine adrenal medulla is screened with the use of the $^{32}$P-labeled cloned PCR product as a probe. In the present invention, 3 plaques are thus obtained and the target cDNA encoding adseverin is assembled on the basis of the overlapping base sequence of these plaques. Thus it is found out that the open reading frame is a protein of 80527 dalton composed of 715 amino acids (see SEQ ID NO: 5 in Sequence Listing).

The cDNA of human adseverin is obtained in the following manner. That is, a double stranded cDNA is synthesized by using TimeSaver™ cDNA Synthesis Kit (Pharmacia).

Then the double stranded cDNA thus synthesized is fractionated in size by using Spun Column included in the above-mentioned Kit or agarose electrophoresis. Thus a cDNA of about 400 bp or more (in the former case) or about 2 to 3 kbp (in the latter case) is taken up exclusively. After ligating an adaptor to one end, the cDNA is integrated into a vector. Then the cDNA thus integrated into the vector is subjected to packaging with the use of GIGAPACK® II PACKAGING EXTRACT (STRATAGENE) to give a cDNA library.

Next, the cDNA library is screened under less stringent conditions by using thermally denatured bovine adseverin cDNA as a probe. Thus one positive phage clone is obtained. Then its cDNA moiety is amplified by PCR and integrated into a plasmid vector to thereby give a clone pADa-17. When partly sequenced, the base sequence of this clone shows a very high homology (80–90%) with the base sequence of the bovine adseverin cDNA. In contrast, it shows only a low homology of 60% or below with gelsolin which is a protein belonging to the adseverin family and having a known base sequence, suggesting that this is a gene obviously different therefrom. Thus it is assumed that this clone is human counter part of adseverin. However, this clone is about 1 kbp in full length and thus seemingly fails to contain the entire coding region. Accordingly, further screening should be carried out.

Thus plaque hybridization is carried out by using the above-mentioned clone pADa-17 as a probe under usual conditions with an elevated strictness. In this step, use is made of a library newly prepared from human kidney mRNA by concentrating cDNAs of 2 to 3 kbp exclusively in order to efficiently obtain clones of the full length. Thus 5 positive phage clones are obtained therefrom and excised into a plasmid [pBluescript® SK(-) vector] with ExAssist™/ SOLR SYSTEM to thereby give plasmid clones phAD-2 to 6. Among these plasmid clones, the base sequences of phAD-2 and phAD-4 are identified. By combining these base sequences, a sequence represented by SEQ ID NO: 6 in Sequence Listing is determined. From this base sequence, an open reading frame composed of 715 amino acids and having ATG at the 79-position as the initiation codon (Met) is found out (SEQ ID NO: 7). FIG. 9 shows the result of a comparison of this amino acid sequence with the bovine adseverin amino acid sequence. These amino acid sequences show a homology of about 92% at the amino acid level, which suggests that this protein has been very well conserved beyond difference in species. It is also clarified that these amino acid sequences are highly analogous in many amino acids, even though they are not completely the same as each other. Although a high homology of about 90% is observed at the base level, the homology shows a rapid decrease after the stop codon, which seemingly reflects the difference in species.

In FIG. 9, putative phospholipid binding sites are boxed by solid lines. The putative phospholipid binding sites in bovine adseverin, namely, (112) KGGLKYKA (119) and (138) RLLHVKGRR (146) are both completely conserved in human adseverin too. Thus it is suggested that the difference in sensitivity to phospholipids between adseverin and gelsolin might be caused by the difference in the amino acid sequences of these regions. It is reported that adseverin is located in cells in the vicinity of cell membrane. Thus, the regulation of the adseverin activity by cell membrane constituents, if any, might be highly important. Since gelsolin is also activated by $Ca^{2+}$, there is a fair possibility that phospholipids would control how to utilize these proteins case by case.

By using the cloned gene of the present invention encoding adseverin thus obtained, adseverin can be produced in a large amount by gene recombination techniques and used for medicinal purposes.

Accordingly, prokaryotic or eukaryotic host cells can be transformed by appropriate vectors into which the gene of the present invention encoding adseverin has been integrated.

Further, the gene can be expressed in each host cell by introducing an adequate promoter or a sequence relating to the expression into these vectors. Moreover, the target gene may be ligated to another gene encoding a polypeptide and expressed as a fused protein to thereby facilitate purification or elevate the expression dose. It is also possible to excise the target protein by effecting adequate treatments in the purification step.

It is generally considered that an eukaryotic gene shows polymorphism as known in the case of human interferon gene. In some cases, one or more amino acids are replaced due to this polymorphism, while changes occur not in amino acids but exclusively in base sequence in other cases.

It is sometimes observed that a polypeptide having the amino acid sequence of SEQ ID NO: 5 or 7 in Sequence Listing having the deletion, addition or replacement of one or more amino acids shows an actin filament-severing activity. For example, it is publicly known that a polypeptide, which is obtained by replacing a base sequence corresponding to cysteine of human interleukin 2 (IL-2) by another base sequence corresponding to serine, sustains the IL-2 activity (Wang et al., Science 224:1431, 1984). Thus the techniques for constructing the variants of these genes encoding adseverin are well known by those skilled in the art.

Moreover, bovine adseverin is highly homologous with human adseverin and highly analogous in many amino acids even though they are not completely the same, as described above. Accordingly, genes having partial replacements of bovine or human adseverin and chimeric genes thereof also fall within the scope of the present invention.

When adseverin is expressed in eukaryotic cells, sugar chain(s) are frequently added thereto and the addition of the sugar chains can be controlled by converting one or more amino acids. In such a case, the expression product sometimes has an actin filament-severing activity. Therefore, the present invention includes any gene which is obtained by artificially varying the gene encoding human adseverin and encodes a polypeptide, so long as the obtained polypeptide has an actin filament-severing activity.

Furthermore, the present invention includes a gene which is capable of giving a polypeptide having an actin filament-serving activity and hybridizable with a gene represented by SEQ ID NO: 4 or 6 in Sequence Listing. The hybridization may be carried out under the conditions commonly employed in probe hybridization (see, for example, Molecular Cloning: A Laboratory Manual, Sambrook et al., Cold Spring Harbor Laboratory Press, 1989).

An expression vector may contain a replication origin, a selective marker, a promoter, an RNA splicing site, a polyadenylation signal, etc.

Examples of the prokaryotic cells to be used as the host cells in the expression system include *E. coli* and *Bacillus subtilis*. Examples of the eukaryotic cells usable as the host cells include yeasts and Myxomycota. Alternatively, insect cells such as Sf9 may be used as the host cells. In addition, use can be made of host cells with an animal origin such as COS cell and CHO cells therefor.

The protein, which has been produced by incubating a transformant transformed by the gene encoding adseverin, can be purified either in the cells or after isolating from the cells.

Adseverin may be isolated and purified by procedures commonly employed in the isolation and purification of proteins. For example, various chromatographies, ultrafiltration, salting out, dialysis, etc. may be adequately selected and combined therefor.

According to the present invention, an antisense DNA can be prepared on the basis of the base sequence of the gene encoding adseverin. The antisense DNA, which has a base sequence complementary to the mRNA, forms base pairs with the mRNA and blocks the transmission of genetic information, thus regulating the synthesis of the adseverin protein, i.e., the final product. The antisense DNA usable in the present invention is an oligonucleotide hybridizable specifically with a base sequence which encodes the amino acid sequence represented by the SEQ ID NO: 5 or 7 in Sequence Listing.

The term "oligonucleotide" as used herein means an oligonucleotide composed of a base occurring in nature with a sugar moiety binding thereto via a phosphodiester bond of the inherent meaning or its analogue. That is to say, the first group meant thereby includes natural oligonucleotides and synthetic oligonucleotides prepared from subunits occurring in nature or homologues thereof. The term "subunit" means a combination of a base with a sugar binding to the adjacent subunit via a phosphodiester bond or another bond. The second group of the oligonucleotide includes analogues of the above-mentioned oligonucleotides taking the same roles as oligonucleotides but having residues containing some parts which are not observed in nature. Oligonucleotides, which have been chemically modified at the phosphate group, the sugar moiety, or the 3'- or 5'-end to enhance the stability, also fall within this category. Examples thereof include oligophosphorothioate and oligomethylphosphonate wherein an oxygen atom in the phosphodiester bond between nucleotides has been replaced respectively by a sulfur atom and —$CH_3$. The phosphodiester bond may be replaced by another structure which in nonionic and non-chiraric. As oligonucleotide analogues, use can be made of those containing modified bases, i.e., purine and pyrimidine which are not observed in nature.

The oligonucleotide to be used in the present invention preferably has 8 to 40, still preferably 15 to 30, subunits.

It is preferable in the present invention that the target part of mRNA, with which the oligonucleotide is hybridized, is the transcription initiation site, the translation initiation site, the intron/exon junction or the 5'-capping site. It is required to select a site free from any strict hindrance by taking the secondary structure of the mRNA into consideration.

The oligonucleotide of the present invention may be prepared by synthesis methods publicly known in the art, for example, the solid phase synthesis with the use of a synthesizer manufactured by Applied Biosystems, etc. It is also possible to prepare other oligonucleotide analogues such as phosphorothioate or alkylated derivatives by using similar methods [Murakami et al., "Kinosei Antisense DNA no Kagaku Gosei (Chemical Synthesis of Functional Antisense DNA)", Yuki Gosei Kagaku (Organic Synthesis Chemistry), 48 (3): 180–193, 1990].

By administering an oligonucleotide hybridizable specifically with the gene of the present invention encoding adseverin to an animal, the formation of adseverin in the animal can be regulated. As described above, adseverin might relate to the multiplication of blood vessel smooth muscles. The multiplication of blood vessel smooth muscles is regarded as one of the factors causing angiostenosis in blood vessel transplantation in bypass operation, etc. or restenosis which is observed at a ratio of 30 to 40% after PTCA. Accordingly, the antisense DNA of the gene encoding adseverin, the administration of which can suppress the multiplication of blood vessel smooth muscles, is usable as a preventive and remedy for these stenoses. For example, it is expected that angiostenosis can be prevented by soaking the blood vessel to be transplanted in a solution containing the oligonucleotide of the present invention to thereby incorporate the oligonucleotide into the cells followed by the transplantation. It is also possible to prevent restenosis by administering the oligonucleotide of the present invention with the use of a PTCA catheter or stent.

An antibody of the present invention capable of recognizing the adseverin protein can be constructed in accordance with a conventional method [see, for example, Shin-seikagaku Jikken Koza (New Biochemistry Experiment Lecture) 1, Tanpakushitsu (Protein) I, 389–397, 1992] by immunizing an animal with adseverin serving as the antigen and collecting and purifying the antibody thus produced in the animal body. The anti-adseverin antibody thus obtained is usable in various immunological assays such as enzyme immunoassays (for example, ELISA), radioimmunoassays and immunofluorescent techniques.

EXAMPLES

To further illustrate the method for obtaining the gene of the present invention encoding adseverin and the expression of this gene in host cells in greater detail, the following Examples will be given. However, it is to be understood that the present invention is not restricted thereto.

Example 1

Isolation and purification of bovine adseverin

Bovine adrenal glands were obtained from a slaughterhouse. All the procedures described below were carried out at 4° C. The adrenal medullae were carefully separated from cortices and minced with scissors. 80 g of the material thus obtained was homogenized in thrice by volume as much buffer A (pH 8.0) containing 40 mM of Tris-HCl, 4 mM of EGTA, 2 mM of EDTA, 1 mM of DTT, 1 mM of DFP, 1 mM of PMSF, $10^{-6}$ M of E-64-c, 10 µg/ml of aprotinin (Trasylol, Bayer) and 0.02% of $NaN_3$ in a Waring blender. The homogenate was centrifuged at 13,000 g at the maximum for 30 minutes. The supernatant was filtered and further centrifuged at 150,000 g at the maximum for 90 minutes. To the supernatant were added 1 mol solutions of $CaCl_2$ and $MgCl_2$ to give final concentrations of 0.5 and 1 mM respectively. Then the resulting solution was passed through a DNaseI-Affi-Gel 15 column which had been equilibrated with buffer B (pH 7.5) containing 50 mM of KCl, 20 mM of Tris-HCl, 0.5 mM of $CaCl_2$, 1 mM of $MgCl_2$, 0.1 mM of PMSF and 0.02% of $NaN_3$. Then the column was washed successively with the buffer B and the modified buffer B containing not 50 mM but 0.6 M of KCl.

Next, $Ca^{2+}$-sensitive proteins were eluted with the modified buffer B containing 10 mM of EGTA as a substitute for 0.5 mM of $CaCl_2$ and eluted with the modified buffer B containing 6 M of urea. Thus 3 $Ca^{2+}$-sensitive actin-binding proteins and actin (molecular weight: 42,000) were eluted with the EGTA-containing buffer. The results of SDS PAGE suggested that these 3 proteins had molecular weights of 86,000, 84,000 and 74,000 respectively (FIG. 1, lanes 1 to 4). The column was regenerated by washing with the buffer B and stored at 4° C.

The EGTA eluate thus collected was adjusted to pH 8.2 with 1 M Tris and then applied to a Q-Sepharose ion exchange column (1.5×12 cm) which had been equilibrated with a solution (pH 8.2) containing 50 mM of KCl, 20 mM of Tris-HCl, 1 mM of EGTA, 0.1 mM of PMSF, 7 mM of 2-mercaptoethanol and 0.02% of $NaN_3$. Proteins were eluted with a linear KCl gradient from 50 to 250 mM and then with 1 M KCl. The first peak fraction corresponding to 0 to 150 mM KCl contained the protein of a molecular weight of 74,000 together with a small amount of contaminating proteins (FIG. 1, lane 6 ). The proteins of molecular weights of 86,000 and 84,000 and actin were contained in the second peak which was the eluate with 1 M KCl (FIG. 1, lane 7).

The fraction containing the protein of a molecular weight of 74,000 was collected, concentrated and applied to a gel filtration HPLC column (TSK-G3000SW, Tosoh) which had been equilibrated with buffer C (pH 7.0) containing 150 mM of NaCl, 20 mM of Tris-HCl, 1 mM of EGTA, 0.1 mM of DTT and 0.02% of $NaN_3$ (FIG. 1, lane 8). The peak fractions were collected and stored on ice.

Example 2

Protease digestion of bovine adseverin
(1) Digestion by Staphylococcus V8 protease Adseverin in digestion buffer C (1 mM of EGTA, 1 mM of DTT, 0.02% of $NaN_3$ and 50 mM of $NH_4HCO_3$) was digested by Staphylococcus V8 protease at room temperature at a ratio of 1:25 (wt/wt). The reaction was stopped by adding 1 mM of DFP followed by SDS-PAGE analysis. Thus it was found out that adseverin was digested into two major fragments of 42,000 and 39,000 in molecular weight. After digesting by the V8 protease over a prolonged period, the fragment of 39,000 in molecular weight was further digested into fragments of molecular weights of 28,000 and 15,000, while the fragment of 42,000 in molecular weight remained stable.

(2) Digestion by trypsin

Adseverin in buffer D (1 mM of EGTA, 1 mM of DTT, 0.02% of $NaN_3$ and 20 mM of Tris-HCL, pH 8.0) was digested by trypsin at a ratio of 1:200. After reacting at 25° C. for 60 minutes, a 200 mM solution of PMSF in ethanol was added to give a final PMSF concentration of 4 mM followed by SDS-PAGE analysis. Thus it was found out that adseverin was also digested into two fragments of 42,000 and 39,000 in molecular weight and no further digestion occurred thereafter.

From the results of recognition reactions of 2 antigelsolin polyclonal antibodies with the above-mentioned 2 fragments, it was confirmed that the fragment of 39,000 in molecular weight was not a digestion product of the fragment of 42,000 in molecular weight.

(3) Purification of V8 protease digestion product

The V8-digestion product was applied to an HPLC DEAE ion exchange column (DEAE-SPW, Tosoh) which had been equilibrated with buffer D. The fragment of 39,000 in molecular weight was adsorbed by the column, while the one of 42,000 in molecular weight was eluted with an NaCl gradient of 0 to 150 mM and obtained as a single peak at the NaCl concentration of 10 mM. Next, the buffer D containing no EGTA but 0.5 mM $CaCl_2$ was used. Thus the fragment of 39,000 in molecular weight was eluted but the fragment of 42,000 in molecular weight was recovered only in a small amount. These 2 V8 protease-digestion fragments thus purified showed almost the same patterns in SDS-PAGE.

(4) Identification of N-terminal amino acid sequence

The N-terminal amino acid sequences of 2 fragments purified in the above (3) and native adseverin were discussed. Although the N-terminal of native adseverin were discussed. Although the N-termini of native adseverin and the fragment of 42,000 in molecular weight were blocked, it was clarified by the Edman degradation method that the vicinity of the N-terminus of the fragment of 39,000 in molecular weight had the following amino acid sequence of SEQ ID NO:1 in Sequence Listing:

KVAHVKQIPFDA.

Figure 2:
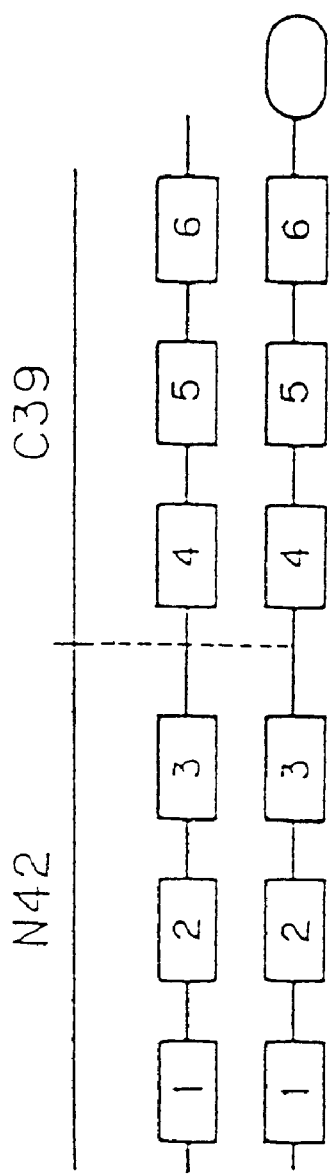
FIG. 2 shows a comparison between the partial amino acid sequence of an adseverin fragment (SEQ ID NO: 1) of a molecular weight of 39,000 (C39) and the amino acid sequences of the corresponding parts of gelsolin (SEQ ID NO:10, residues 413–424) and chicken villin (SEQ ID NO:PB 18).

This sequence was compared with those of publicly known actin filament-serving proteins gelsolin (Kwiatkowski et al., Nature 323:455–458, 1986) and villin (Bazari et al., Proc. Natl. Acad. Sci. U.S.A. 85:4986–4990, 1988). As a result, the above-mentioned sequence was similar to the hinge region located between the conserved repetition segments 3 and 4 in gelsolin and villin, i.e., the middles of these molecules, as shown in FIG. 2. Thus, it is suggested that the fragment of 42,000 in molecular weight is a protein located in the $NH_2$-terminal half of adseverin (hereinafter referred to as "N42"), while the fragment of 39,000 in molecular weight is a protein located in the COOH-terminal half of adseverin (hereinafter referred to as "C39").

(5) Actin-binding properties of N42 and C39

The actin-binding properties of N42 and C39 obtained above were examined by using an actin monomer (G-actin) bound to agarose beads. As a result, it was clarified that N42 and C39 both bound to G-actin in the presence of calcium but not in the absence of calcium.

(6) Identification of functional domain of adseverin (digestion of N42 by thermolysin)

When N42 was digested by thermolysin which was a metaproteinase, 5 fragments including those of 31,000, 30,000 and 16,000 in molecular weight and 2 different ones of 15,000 in molecular weight were obtained. These fragments were purified by HPLC. The fragments of 31,000 and 30,000 in molecular weight were named respectively TL1 and TL2, while the other 3 fragments were named TL3 (molecular weight: 16,000), TL4 (molecular weight: 16,000) and TL5 (molecular weight: 15,000) in the order of elution from the HPLC column. The N-termini of TL1 and TL3 were not detected by an antibody A, since they were blocked as in the case of N42 and native adseverin. On the other hand, TL2 and TL5 reacted with the antibody A. Based on these results, it is estimated that N42 has 2 cleavage sites with the mapping of the fragment as shown in FIG. 3.

Figure 3:
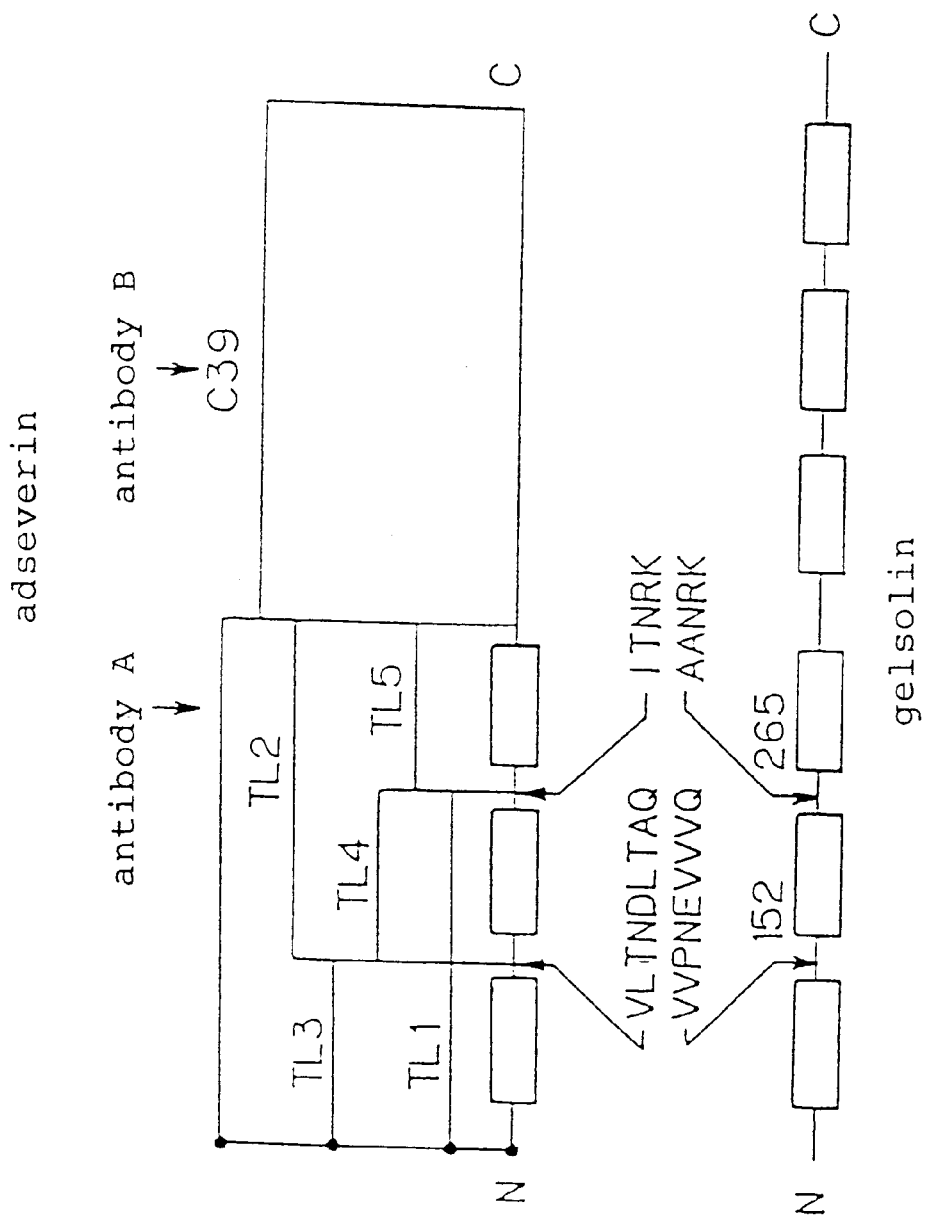
FIG. 3 shows the amino acid sequence of the N-terminus of a fragment obtained by digesting adseverin with thermolysin (SEQ ID NO: 10, residues 179–187 and 292–296) and the predicted location thereof in comparison with gelsolin (SEQ ID NO:5, residues 129–137 and 243–247).

The amino acid sequences of TL4 and TL5, the N-termini of which were not blocked, were analyzed by the Edman degradation method. As a result, it is proved that the N-terminal amino acid sequence of TL4 is the following one represented by SEQ ID NO:2 of Sequence Listing:

VLTNDLTAQ which is homologous with the sequence of the hinge region between the segments 1 and 2 of gelsolin. On the other hand, the N-terminal amino acid sequence of TL5 is the following one represented by SEQ ID NO:3 of Sequence Listing:

ITNRK which is homologous with the sequence of the hinge region between the segments 2 and 3 of gelsolin (FIG. 3).

Accordingly, it is considered that adseverin has a structure similar to that of gelsolin. Similar to gelsolin, the N-terminal half of adseverin is composed of 3 repetition segments each corresponding to a protein digestion fragment of up to 15 kDa.

Example 3

Synthesis of Degenerate Primers

Mix primers, which contained all codons potentially serving as genes encoding the N-terminal amino acid sequence of the second segment (S2) of N42 identified in Example 2 and the N-terminal amino acid sequence of C39, were synthesized by using an Applied Biosystems 380B DNA synthesizer. To the 5' ends of the sense and antisense primers, BamHI site and ClaI site were added respectively.

The sequences of the degenerate primers were as follows:

5'. . . GATGCGGATCCAA(C/T)GA(C/T)(C/T)T(A/C/G/T)AC(A/C/G/T)GC(A/C/G/T)CA . . . 3' (SEQ ID NO:12); and 5'. . . GATGCATCGATAC(A/G)TG(A/C/G/T)GC(A/C/G/T)AC(C/T)TT(C/T)TC . . . 3' (SEQ ID NO:13);

Example 4

Reverse Transcription and PCR

RNA was prepared in accordance with the method of Chirgwin et al. (Biochemistry 18:5294–5299, 1979) from MDBK cells, i.e., a cell line established from bovine kidney (JCRB-Cell, obtained from Japan Foundation for Cancer Research: Madin et al., Proc. Soc. Exp. Biol. Med. 98:574–576, 1958).

Reverse transcription and PCR were carried out in accordance with the method of Kawasaki [in PCR protocols: A guide to Methods and Application (Innis et al. eds) pp.

21–27, Academic Press, San Diego, 1990]. Random hexamers (Pharmacia) were employed for the reverse transcription, while the degenerate primers obtained in Example 3 were employed for PCR [Lee et al., in PCR protocols: Guide to Methods and Application (Innis et al. eds) pp. 46–53, Academic Press, San Diego, 1990]. PCR was effected first in 5 cycles each consisting of 1 minute at 94° C., 1 minute at 37° C. and 2 minutes at 72° C., wherein the treating temperature was slowly elevated from 37 to 72° C. for 2.5 minutes. Next, 29 cycles each consisting of 1 minute at 94° C., 1 minute at 50° C. and 2 minutes at 72° C. were repeated in a usual manner followed by 1 cycle consisting of 1 minute at 94° C., 1 minute at 50° C. and 10 minutes at 72° C. Then the reaction mixture was allowed to stand at 4° C.

Example 5

Cloning of PCR Product

The PCR product obtained in Example 4 was electrophoresed on a 1% agarose gel containing 1 μg/ml of ethidium bromide. As a result, the main band was observed at about 700 bp. Then it was excised from the gel and purified with the use of a GENECLEAN II Kit (BIO 101 Inc.). Its size could be estimated depending on the locations of the fragments from which the degenerate primers were derived, on the basis of an assumption that adseverin might be highly homologous with gelsolin in the primary structure. The product thus purified was digested with BamHI and ClaI and cloned into pBluescript SK(−) (Stratagene).

When the clones PCR product was sequenced, a nucleotide sequence encoding the N-terminus of the third segment (S3) of N42 was contained therein. Thus it was confirmed that this PCR product actually corresponded to a part of the adseverin cDNA. The high homology (identity at nucleotide level: 64%) between this sequence and the human gelsolin sequence also supported this idea.

The PCR product thus obtained was $^{32}$P-labeled and employed as a probe in the subsequent screening.

Example 6

Library Screening

A λgt11 cDNA library prepared from bovine adrenal medulla (CLONETECH) was screened in accordance with the standard method (Sambrook et al., Molecular Cloning: A Laboratory Manual, 2nd Ed., Cold Spring Harbor Laboratory, Cold Spring Harbor, New York, 1989) with the use of the $^{32}$P-labeled PCR product obtained in Example 5 which represented the partial cDNA of adseverin. After screening twice, well-isolated positive plaques were taken out and phages in each plaque were released into 200 μl of distilled water and incubated at room temperature for 1 hour. Then the phage solution was frozen, thawed and heated at 90° C. for 10 minutes.

By using an appropriate amount of the phage solution as a template, the insert of the recombinant phage DNA was amplified by PCR with the use of a pair of primers which contained sequences from the upstream and downstream of the EcoRI-specific site of λgt11. PCR was carried out under the same conditions as those described in Example 4. To the 5'-ends of these primers, XhoI site and NotI site were respectively added. One of the primers had the following sequence:

5'. . . AdseverinCTCGAGGGTGGCGACGACTCC . . . 3'(SEQ ID NO:14); and another one had the following sequence:

5'. . . AdseverinGCGGCCGCTTGACACCAGACCAA . . . 3'(SEQ ID NO:15).

After the completion of PCR, the reaction product was electrophoresed on a 1% agarose gel. The amplified insert DNA was excised and purified by using a GENECLEAN II kit. After digesting with XhoI and NotI, the insert cDNA was cloned into pBluescript SK(−) which had been digested with XhoI and NotI.

By using the cloned PCR product as a probe, the cDNA library of bovine adrenal medulla was screened. Thus 3 overlapping cDNA clones were plaque-purified from 2×10$^6$ recombinant phages.

Figure 4:
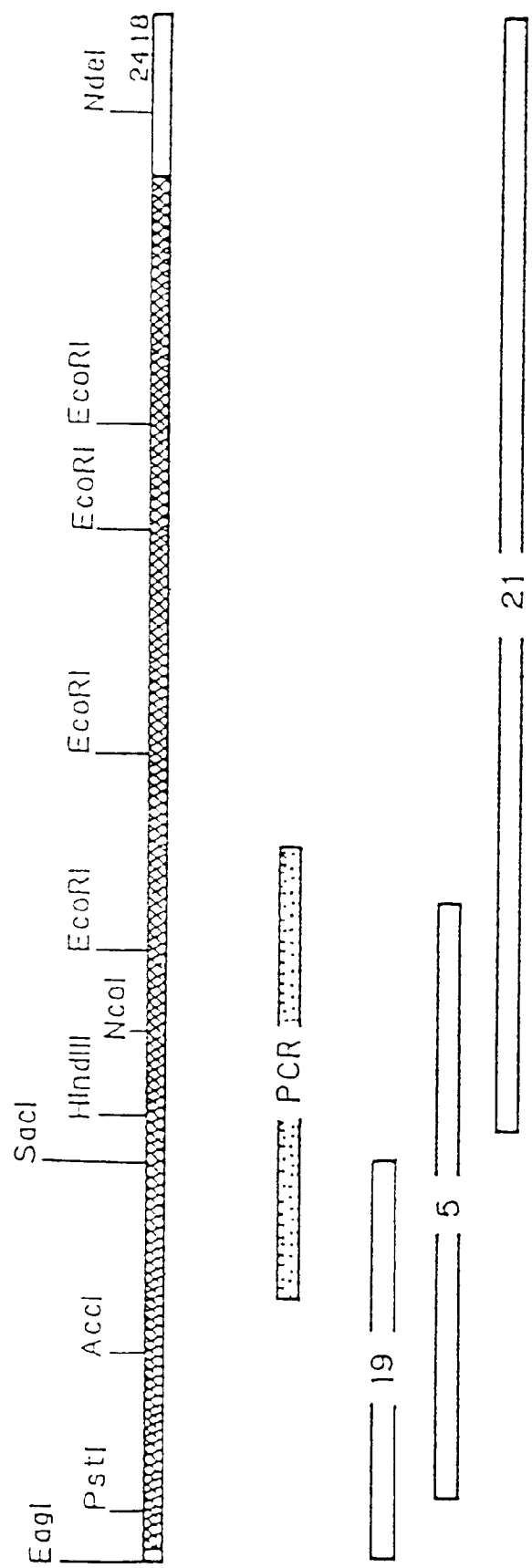
FIG. 4 shows a restriction map of bovine adseverin cDNA. The bar designated as PCR stands for the cDNA produced by the reverse transcription from RNA of MDBK cells and PCR. The open bars numbered 19, 5 and 21 stand for individual cDNA clones isolated from the λgt11 cDNA library of bovine adrenal medulla and employed in the construction of the adseverin cDNA.

The above-mentioned 3 cDNA clones overlapping each other are shown by Nos. 19, 5 and 21 in FIG. 4. The base sequences of these cloned DNAs were examined in both directions by the dideoxy chain termination method (Sanger et al., Proc Natl. Acad. Sci. U.S.A., 74:5463–5467, 1977) and the entire nucleotide sequence of adseverin was identified based thereon. This nucleotide sequence is represented by SEQ ID NO:4 in Sequence Listing. FIG. 4 shows a restrictionmap of the cDNA thus assembled.

The nucleotide sequence of the assembled cDNA and the amino acid sequence corresponding to the longest open reading frame are also represented by SEQ ID NO:4 in Sequence Listing. The open reading frame encodes a protein of 80527 dalton, consisting of 715 amino acids. The first ATG is located on 27 nucleotides 3'-side to the start of the clone and represents a good vertebrae translation initiation consensus sequence. A comparison of the adseverin cDNA sequence with the sequences of gelsolin and villin also supports that the ATG represents the initiation codon and that the assemble cDNA contains the entire coding sequence of adseverin.

Next, a cDNA of 2418 bp which contained the entire coding region of adseverin was assembled from the 3 overlapping clones with the use of AccI and HindIII sites. This cDNA was integrated into the XhoI and NotI sites of pBluescript SK(−) to thereby give pSK-adseverin.

Example 7

Figure 5B:
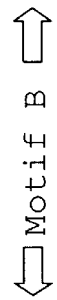
Figure 5C:
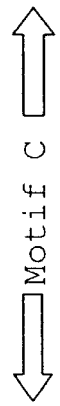
Figure 5E:
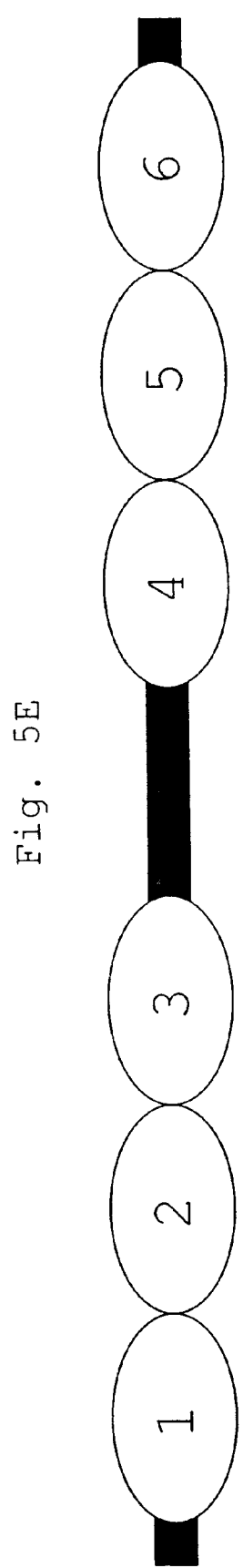

Comparison of Predicted Amino Acid Sequence of Adseverin with Amino Acid Sequences of Human Gelsolin and Villin Biochemical analyses and the predicted amino acid sequence from cDNA have revealed that human gelsolin and villin each consists of 6 homologous segments. (Bazari et al., Proc. Natl. Acad. Sci. U.S.A. 85:4986–4990, 1988; Matsidaora et al., Cell 54:139–140, 1988; Way et al., J. Mol. Biol. 203:1127–1133, 1988). The segments 1, 2 and 3 have higher homologies respectively with the segments 4, 5 and 6 than nay other combinations. The analysis on the predicted amino acid sequence of adseverin has revealed that adseverin has 6 homologous segments too. The segments 1 to 6 have homologies respectively with the corresponding segments of gelsolin and villin (FIG. 5). As FIG. 5 clearly shows, motifs B, A and C existing in each of the 6 segments of gelsolin and villin were also found out in the 6 segments of adseverin. These facts indicate that adseverin belongs to gelsolin family proteins.

Moreover, the putative polyphosphoinositide binding sequences existing in gelsolin and villin were also found in adseverin in the regions corresponding to the regions of gelsolin and villin, i.e., the first and second segments (S1, S2). This fact agrees with the data that the protein fragment-severing activity corresponding to S1–2 of adseverin was inhibited by polyphosphoinositide. These sequences are boxed in FIG. 5 and shown as a model view in Table 1. One of these 2 putative sequences completely agreed with the consensus sequence, while another one located in the first segment was different from the consensus sequence only in one amino acid. That is to say, it had alanine at the COOH-terminal while the consensus sequence had a basic amino acid at this position. Thus this domain of adseverin had a less basic nature than that of the corresponding domain of gelsolin. This difference could partly account that acidic phospholipids other than phosphatidylinositol 4,5-bisphosphate and phosphatidylinositol 4-monophosphate, for example, phosphatidylinositol and phosphatidylserine can inhibit the serving activity of adseverin but not that of gelsolin.

TABLE 1

Predicted polyphosphoinositide binding sites of adseverin in comparison with other actin filament-severing proteins

| Protein | Location of binding site | Amino acid sequence |
|---|---|---|
| adseverin | 112–119 (SEQ ID NO:5) | KGG-LKYKA |
| gelsolin | 135–142 (SEQ ID NO:10) | KSG-LKYKK |
| villin | 112–119 (SEQ ID NO:11) | KQG-LVIRK |
| adseverin | 138–146 (SEQ ID NO:5) | RLLHVKGRR |
| gelsolin | 161–169 (SEQ ID NO:10) | RLFQVKGRR |
| villin | 138–146 (SEQ ID NO:11) | RLLHVKGKR |
| consensus | | K    KK |
| | | XX(X)XKX |
| | | R    RR |

Example 8

Expression of Adseverin cDNA in *E. coli*

Figure 6:
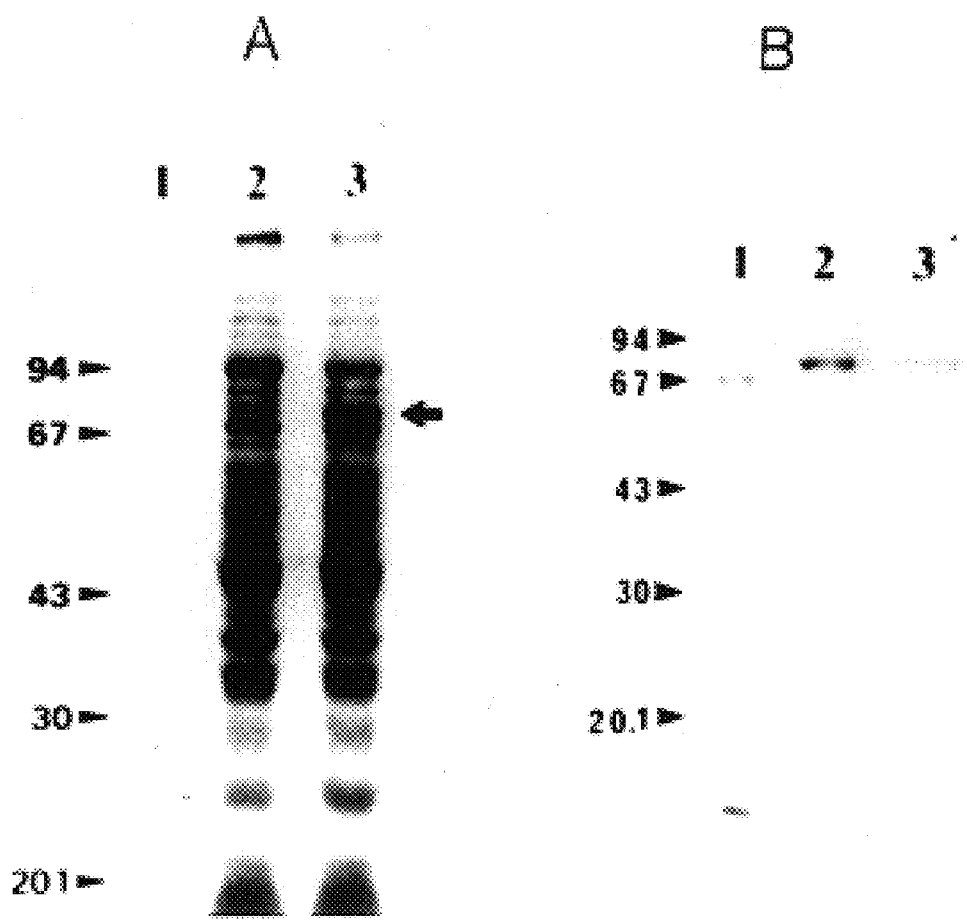
FIGS. 6A–6B are photographs which shows the electrophoretic pattern of the expression of adseverin in *Escherichia coli* and purification thereof.

The bovine adseverin cDNA (pSK-adseverin) obtained in Example 6 was amplified by PCR. Primers empoloyed in PCR were so designed that the initiation codon (ATG) of the product cDNA constituted a part of NdeI while the termination codon (TAA) was immediately followed by the XhoI site. The cDNA thus obtained was integrated into an expression vector pET-23a (Novagen) via the NdeI and XhoI sites. The resulting recombinant vector pET-adseverin was then introduced into competent BL21(DE3)pLysS cells by the method of Chung et al. (Proc. Natl. Acad. Sci. U.S.A. 86:2172–2175, 1998). Transformants were selected, incubated and induced with IPTG (isopropyl-β-thiogalactopyranoside) in accordance with the method of Studier et al. [in Methods in Enzymology, Gene Expression Technology (Goeddle eds) Vo., 185, pp. 60–89, Academic Press, San Diego, 1991]. Namely, a colony resistant against ampicillin and chloramphenicol was picked up and incubated in M9ZB medium supplemented with 50 μg/ml of ampicillin. When the expression of the cDNA was induced by IPTG, a protein of approximately 74 kDA on SDS-PAGE was produced (FIG. 6A, indicated by arrow). In contrast, the untransformed control BL21(DE3) pLysS produced no extra protein on the induction with IPTG. The size (i.e., 74 kDa) of the induced protein on SDS-PAGE was the same as that of adseverin prepared from bovine adrenal medulla.

The culture supernatant of the transformed *E. coli* was purified by substantially the same methods the one employed for the isolation and purification of adseverin from bovine adrenal medulla in Example 1. The purified protein was electrophoresed on SDS-PAGE and transferred onto a nitrocellulose membrane. When reacted with an antibody specific to adseverin, this protein underwent an immunological reaction with this protein, as shown in FIG. 6B. Based on the apparent size of this protein on SDS-PAGE and its immunoreactivity with the adseverin specific antibody, it was confirmed that this protein was the cDNA encoding adseverin.

Example 9

Actin Filament-severing Activity of Adseverin Produced by *E. coli*

To examine whether or not the adseverin produced by *E. coli* had a $Ca^{2+}$-dependent actin filament-severing activity similar to native adseverin, effects of the adseverin on actin polymerization were measured with a viscometer.

0.15 mg/ml of actin was polymerized in buffer P (50 mM KCl, 2 mM $MgCl_2$ and 20 mM imidazole-HCl, pH 7.2) with 1 mM of EGTA or 0.1 mM of $CaCl_2$ at 25.5° C. in the presence or absence of adseverin at a molar ratio to actin of 1:30.

Figure 7:
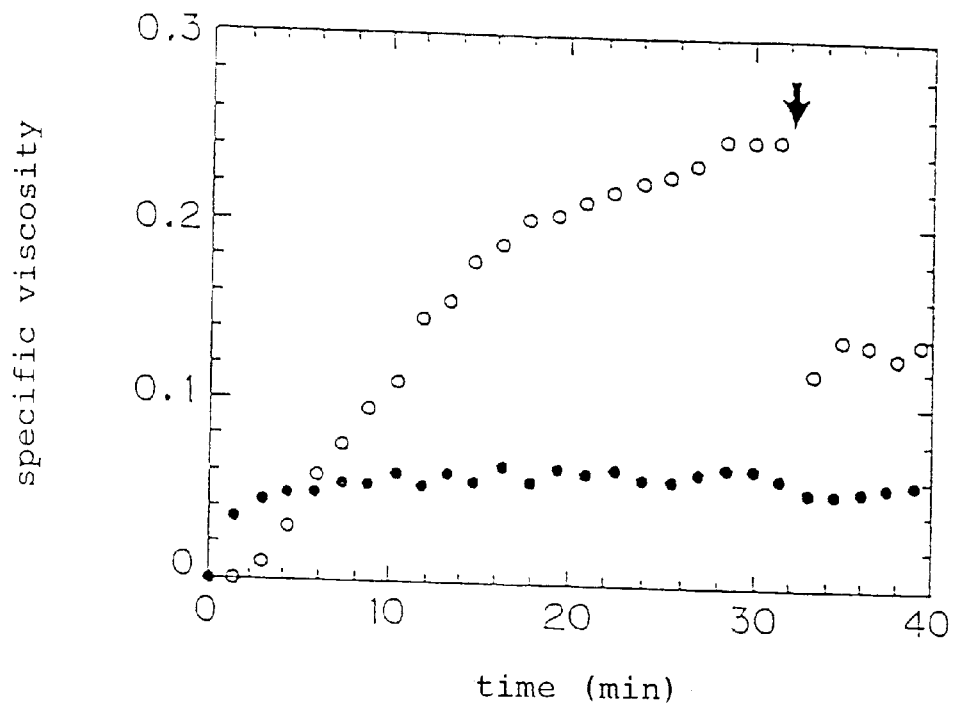
In FIG. 7, the data expressed in ○ and △ indicate the results of the polymerization in the presence of actin alone, while the data expressed in ● and ▲ indicate the results of the polymerization in the presence of the adseverin added at a molar ratio to actin of 1:30. The adseverin was added to the actin solution at a molar ratio of 1:30 at the points indicated by the arrows.
Figure 7:
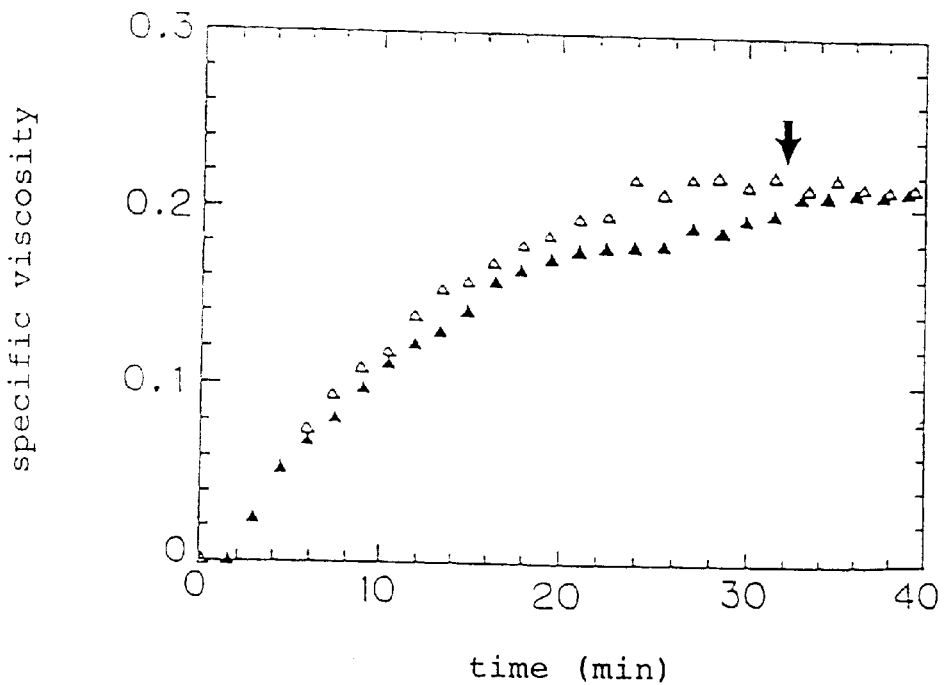

As FIG. 7 shows, the viscosity of the actin solution was affected by adseverin exclusively in the presence of $Ca^{2+}$ (compare FIG. 7A with 7B). In the presence of $Ca^{2+}$, adseverin promoted the nucleation in the process of actin polymerization so as to lower the final viscosity of the polymerized actin solution. When adseverin was added to the polymerized actin solution (indicated by arrows), the specific viscosity showed a sudden drop in the case of the solution containing $Ca^{2+}$.

These results were substantially the same as those obtained by using adseverin prepared from bovine adrenal medulla, which indicated that the protein produced by the gene recombinaiton techniques according to the present invention had an actin filament-severing activity similar to native adseverin.

Example 10

In situ Hybridization

A 329 bp fragment of the bovine adseverin cDNA (#2090–#2418) was labeled with digoxigenin-dUTP by using a DIG DNA labeling and detection kit (Boehringer Mannheim).

The part of fresh bovine adrenal gland containing the interface region between cortex and medulla was fixed with 1% paraformaldehyde in phosphate saline buffer (PBS) in the slaughterhouse. In the laboratory, it was cut into small pieces and washed with PBS. Next, the samples were immersed stepwise in 8, 12, 16 and 20% sucrose-PBS for 24 hours. Then the samples were embedded in TISSUE-TEM (Miles Scientific) and frozen in liquid nitrogen. The frozen samples were cut into sections of 5 to 7 μm with a microtome and collected on a slide glass.

Some of these sections were stained with 0.5% of Toluidine Blue in PBS and 50% of glycerol in PBS and stored in this solution.

For immunofluorescent staining, the sections were fixed with 1% paraformaldehyde-PBS for 1 minute and with acetone for 5 minutes. After treating with 1% of Triton X-100 in PBS and washing with PBS, the sections were introduced into a blocking solution containing 2.5% of bovine serum albumin and 2.5% of chick serum in PBS and incubated together with anti-adseverin antibody (method for the preparation of the anti-adseverin antibody will be described in Example 18 hereinafter) in the blocking solution at 37° C. for 3 hours. Then the sections were washed successively with a solution containing 400 mM of MgCl$_2$ and 20 mM of Tris-HCl (pH 8.6) and PBS. Then they were incubated together with FITC-conjugated anti-rabbit IgG in the blocking solution at 37° C. for 1 hour. After thoroughly washing by the same procedure with the use of the same solutions as those described above, the sections were embedded in PBS containing 50% of glycerol and 2.5% of 1,4-diazabicyclo[2,2,2]octane (Wako Chemical Co., Ltd.) and observed under a Nikon FEX-A fluorescent microscope.

For in situ hybridization, the sections were incubated in double strength standard saline citrate (2×SSC, 1×SSC=0.15 M NaCl, 15 mM Na-citrate, pH 7.0) for 10 minutes at room temperature and then in a pre-hybridization solution (5×SSC, 50% formamide, 0.1% Tween 20, 50 µg/ml heparin, 100 g/ml sonicated and denatured salmon sperm DNA) at room temperature for 1 hour.

After removing the pre-hybridization buffer, a fresh pre-hybridization buffer containing 0.5 µg/ml of the digoxigenin-labeled DNA probe was applied to the sections. Then the sections were covered with glass cover slips which were next sealed with rubber cement.

The DNA probe was denatured in an oven at 80° C. for 10 minutes followed by incubation in the oven at 42° C. overnight. Then the cover slips were removed by using a glass cutter and the sections were washed successively with 2×SSC at room temperature for 30 minutes, 0.1×SSC at 42° C. for 30 minutes and 2×SSC at room temperature for 15 minutes.

The probes in the sections were detected by using a DIG DNA labeling and detection kit (Boehringer Mannheim). Then the sections incubated together with the digoxigenin-labeled DNA probe were washed in a washing buffer (100 mM Tris-HCl, 150 mM NaCl, pH 7.5) at room temperature for 10 minutes, then incubated together with 0.5% (w/v) of Boehringer blocking reagent in the washing buffer and finally washed with the washing buffer.

Subsequently, the sections were incubated together with alkaline phosphatase-conjugated anti-digoxigenin antibody (150 mU/ml) at 37° C. in the dark for 2 hours. After washing with the washing buffer twice, the slides were briefly treated with a solution containing 100 mM of Tris-HCl, 100 mM of NaCl and 20 mM of MgCl$_2$ (pH 9.5) and incubated together with the same solution containing nitro blue tetrazolium salt, 5-bromo-4-chloro-3-indolyl phosphate and 0.25 mg/ml of levamisole at room temperature in the dark for 3 hours. The color development was stopped by using 10 mM of Tris-HCl and 1 mM of EDTA (pH 8.0).

The sections kept in glycerol were observed under a light microscope.

Figure 8:
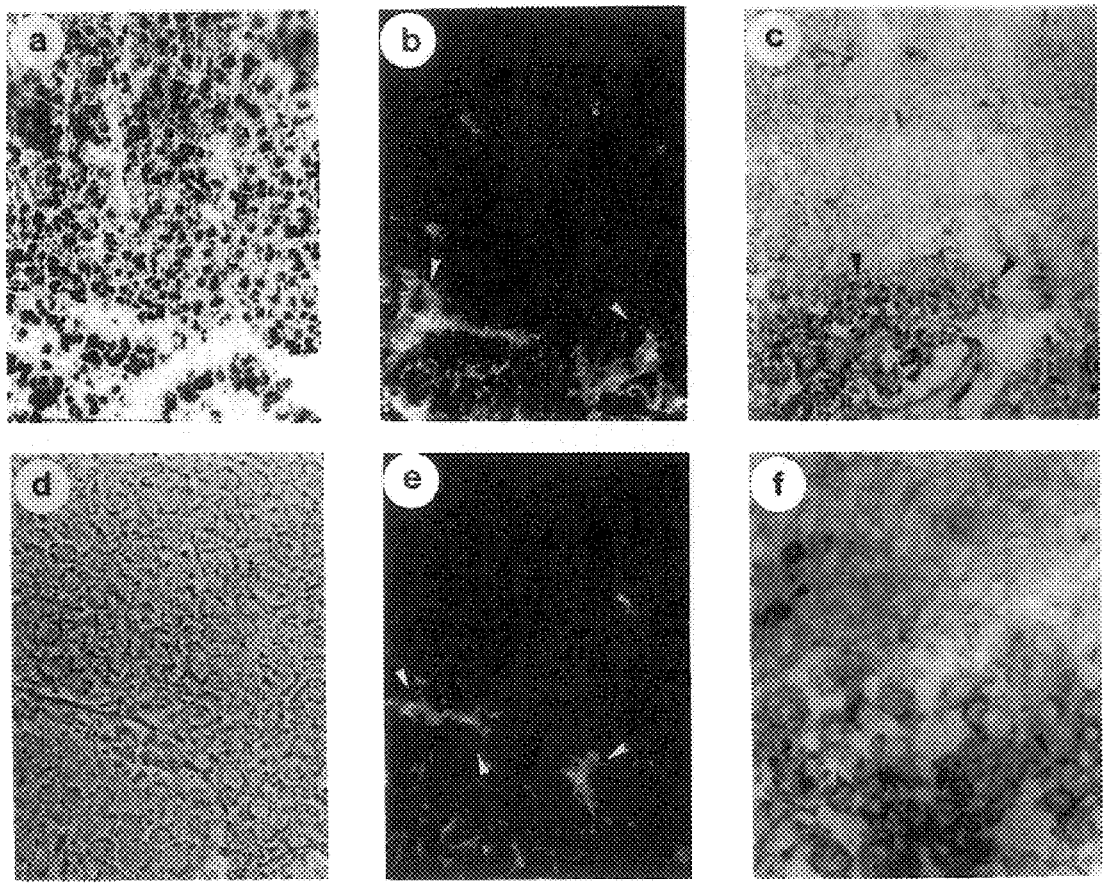
FIGS. 8a–8f provide light microscopic photographs, which show the morphology of organisms, of the expression of adseverin and its mRNA in the interface area between cortex and medulla of bovine adrenal gland. In each photograph, the upper part corresponds to the cortex while the lower part corresponds to the medulla. The sections were stained with Toluidine Blue (panel 8a) or successively with anti-adseverin rabbit antibody and fluorescein-conjugated anti-rabbit immunoglobin (panels 8b and 8e). Panel 8d shows a phase-contrast image of the same field as the one of the panel 8e. Panels 8c and 8f show the images of in situ hybridization. The panels 8a and 8c are given in 120× magnification, while the panels 8d to 8f are given in 280× magnification.

At a low magnification, the color development was observed in the medulla but not in the cortex except in the area adjacent to the medulla. Next, the interface area between the medulla and the cortex was observed at higher magnifications. Toluidine Blue staining (FIG. 8a) revealed that the cells in the cortex were tightly packed, whereas the cells in the medulla were loosely distributed and classified into groups by sheath-like structures containing vessels. The cortex and the medulla were easily distinguishable from each other in both of the in situ hybridization and the immunofluorescent staining depending on the cellular characteristics as described above without effecting counterstaining. FIG. 8c and f show the results of the in situ hybridization observed at middle and high magnifications respectively. Staining was observed mainly in loosely packed cells corresponding to the medullary chromaffin cells. In addition, a small number of cells in the cortex facing the medulla were also stained as shown by arrows.

The adseverin distribution of the same pattern was observed in the immunofluorescent staining with the anti-adseverin antibody (FIG. 8b and e). Namely, fluorescence was observed in the chromaffin cells of the medulla and in the cells in the cortex facing the medulla. In the chromaffin cells, fluorescence was mainly observed in the subplasmalemmal region.

In summary, it was demonstrated that the adseverin mRNA and the adseverin protein were both expressed in the adrenal medulla but not in most part of the cortex. Exceptionally, the expression of both of the adseverin mRNA and the adseverin protein was observed in a part of the cortex facing the medulla. Thus it is concluded that such differential expression of adseverin in the parts of bovine adrenal glad is controlled at the transcription level. Secretion in the mode of exocytosis takes place in the adrenal medulla but not in the adrenal cortex. Therefore, this differential expression strongly suggests that adseverin relates not to the regulation of the secretory process in general but exclusively to the secretory process depending on the mode of exocytosis. Further, the localization of adseverin in the subplasmalemmal region agrees with the idea that this protein relates to the regulation of exocytosis.

Example 11

Construction of cDNA Library Originating in Human Kidney mRNA

As the human kidney mRNA, use was made of a product purchased from CLONTECH Laboratories, Inc. From 2 µg of this mRNA, double stranded cDNAs were synthesized by using TimeSaver™ cDNA Synthesis Kit (Pharmacia) in accordance with the attached protocol.

Namely, the thermally denatured mRNA was added to First-Strand Reaction Mix containing murine reverse transcriptase and oligo(dT)$_{12-18}$ primers and kept at 37° C. for 1 hours to thereby synthesize the first strand. Next, the reaction mixture was added to Second-Strand Reaction Mix containing E. coli RNAaseH and E. coli DNA polymerase I and kept at 12° C. for 30 minutes and then at 22° C. for 1 hour to thereby synthesize the second stand. Then the double stranded cDNA thus synthesized was fractionated in size by using Spun Column included in the above-mentioned kit or agarose electrophoresis. Thus a cDNA of about 400 bp or mroe (in the former case) of about 2 to 3 kbp (in the latter case) was taken up exclusively.

After ligating an adaptor (EcoRI/NotI adaptor) to one end and eliminating the unreacted adaptor with the above-mentioned Spun Column, the cDNA was integrated into a vector. Two vectors were prepared therefor, namely, ExCell vector (λExCell EcoRI/CIP) purchased form Pharmacia and Lambda ZAP®II vector (PREDIGESTED LAMBDA ZAP®II/EcoRI/CIAP CLONING KIT) purchased from STRATAGENE. As the host E. coli, NM522 strain was used in the former case while XL1-Blue strain was used in the latter case. Then the cDNA thus integrated into the vector was subjected to packaging with the use of GIGAPACK® II PACKAGING EXTRACT (STRATAGENE) in accordance with the attached protocol. Namely, Freeze/Thaw extract, Sonic extract and the DNA were mixed and kept at 22° C. for 2 hours to give a cDNA library.

Example 12 cDNA Library Screening by Plaque Hybridization (Hybridization with the Use of Bovine Adseverin cDNa as Probe)

Screening was carried out by reference to the standard method described by Samborrk, J., Fritsch, E. F. and Maniatis, T., Molecular Cloning, Cold Spring Harbor Lab. (1988). Namely, phage plaques grown on an LB agar plate were transcribed onto a Hybond-N filter (Amersham), denatured with an alkali and then immobilized by UV irradiation. Pre-hybridization was effected by keeping this filter in a hybridization solution at 40° C. for 3 hours. Subsequently, hybridization was effected by keeping the filter together with a $^{32}$P-labeled, thermally denatured probe (about 1 μCi/ml) at 40° C. for 16 hours. As a probe, use was made of a fragment excised from bovine adseverin cDNA (pSK-adseverin) with the use of PstI and NdeI and corresponding to almost the full length of the cDNA. The hybridization was effected under less stringent conditions, i.e., by using a hybridization solution containing 25% of formaide (4×SSC, 50 mM HEPES, pH 7.0, 10×Denhardt'solution, 100 μg/ml thermally denatured salmon sperm) (Institute of Medical Science, University of Tokyo, Carcinostatic Research Section, "Shin Saibo Kogaku Jikken Purotokoru (New Protocols for Cell Technological Experiments)", Saibo Kogaku (Cell Technology), 1993]. After the completion of the hybridization, the filter was washed with a 2×SSC solution containing 0.1% of SDS at room temperature for 15 minutes twice. Next, it was further washed with a 1×SSC, 0.1% SDS solution with slowly elevating temperature from room temperature until the background radioactivity disappeared. Then the filter was dried followed by autoradiography.

The probe was labeled with $^{32}$P by using a Random Primer DNA Labeling Kit Ver. 2 (Takara Shuzo Co., Ltd.). In accordance with the attached protocol, about 100 ng of thermally denatured DNA was labeled by keeping at 37° C. for 30 minutes together with the random primer 50 μCi[α-$^{32}$P] dCTP and Klenow fragment.

First, 1.6×10$^5$ plaques of the cDNA library constructed from the human kidney mRNA obtained in Example 11 were screened with the use of the bovine adseverin cDNA as a probe. Thus a positive phage clone was obtained.

Example 13

Subcloning of Positive Phage Clone into Plasmid Vector

By using primers (CAGCTATGACCATGATTACGCCAA (SEQ ID NO:16) ACGACGGCCAGTGAATTGCGTAAT (SEQ ID NO:17)) synthesized from the base sequence of the λExCell vector, the insert of the clone obtained in Example 12 was amplified [Institute of Medical Science, University of Tokyo, Carcinostatic Research Section, "Shin Saibo Kogaku Jikken Purotokoru (New Protocols for Cell Technological Experiments) ", Saibo Kogaku (Cell Technology), 1993], and cleaved with EcoRI. Then it was subcloned into the pUC18 plasmid vector which had been cleaved with EcoRI and dephosphorylated. The clone thus obtained was named pADa-17.

Example 14 cDNA Library Screening by Plaque Hybridization (Hybridization with the Use of pADa-17 as Probe)

By using a library newly constructed from the human kidney mRNA in accordance with the method of Example 11 and having cDNAs of 2 to 3 kbp exclusively concentrated therein, plaque hybridization was carried out with using the clone pADa-17 as a probe and increasing the strictness (50% formamide-containing hybridization solution: other composition being the same as the one of Example 12) under the conventional conditions. The vector employed for the construction of the cDNA library was Lambda ZAP® II vector (PREDIGESTED LAMBDA ZAP® II/EcoRI/CIAP CLONING KIT) purchased from STRATAGENE, while XLI-Blue strain was employed as the host E. coli. The probe was labeled with $^{32}$P in the same manner as the one described in Example 12. Namely, a fragment excised from the clone pADa-17 was electrophoresed on an agarose gel and purified and about 100 ng thereof was labeled with 50 μCi of [α-$^{32}$P] dCTP. After the completion of the hybridization, the filter was washed with a 2×SSC solution containing 0.1% of SDS at room temperature for 15 minutes twice. Next, it was further washed with a 0.5×SSC, 0.1% SDS solution at 50° C. for 15 minutes twice. Then the filter was dried followed by autoradiography.

Thus 5 positive phage clones were obtained by screening 1.7×10$^5$ plaques.

Example 15

Subcloning of Positive Phage Clone into Plasmid Vector

From the positive phage clones, excision was carried out into a plasmid [pBluescript® SK(−) vector] with the use of ExAssist™/SOLR™ SYSTEM by taking advantage of the characteristics of the Lambada ZAP® II vector. In accordance with the protocol attached to PREDIGESTED LAMBDA ZAP® II/EcoRI/CIAP CLONING KIT (STRATAGENE), E. coli XL-1Blue strain was infected with the positive phages obtained in Example 14 and the ExAssist™ helper phage and incubated at 37° C. for 2.5 hours. Then the plasmid excised into the culture medium were incorporated into E. coli SOLR strain. Thus plasmid clones phAD-2 to 6 were obtained.

Example 16

Identification of Base Sequence of Human Adseverin cDNA

The base sequences of the plasmid clones phAD-2 and phAD-4 obtained in Example 15 were identified. The base sequences were identified by performing dideoxy sequencing with the use of Sequence Version 2.0 (United States Biochemical) or by the cycle sequencing with the use of PRISM™ Terminator Mix (Applied Biosystems) and coding with the use of a Model 373A sequencer (Applied Biosystems).

The base sequence of human adseverin cDNA obtained by assembling the base sequences of phAD-2 and phAD-4 identified above and the amino acid sequence corresponding to the longest open reading frame are shown in SEQ ID NO: 6 in Sequence Listing. Thus an open reading frame, which had the initiation codon at ATG at the 79-position and was composed of 715 amino acids, was found out.

Example 17

Comparison of Human Adseverin with Bovine Adseverin

FIG. 9 shows the result of a comparison between the amino acid sequence of human adseverin obtained in Example 16 and the amino acid sequence of bovine adseverin obtained in Example 6. In FIG. 9, the upper and lower columns correspond respectively to the human amino acid sequence and the bovine amino acid sequence. These amino acid sequences are completely identical with each other at the amino acids with the mark * and highly analogous at the amino acids with the mark. The human adseverin and the bovine adseverin show a homology of about 92% at the amino acid level and are highly analogous in many amino acids even though they are not completely the same. Although a high homology of about 90% is observed at the base level too, the homology shows a rapid decrease after the stop codon.

Example 18

Preparation of Anti-adseverin Antibody and Anti-peptide Antibody (Antibody Against Human Adseverin-derived Peptide)

PREPARATION OF ANTI-ADSERVERIN ANTIBODY 1 mg of adseverin purified from bovine adrenal medulla was mixed with Freund's complete adjuvant to thereby give an emulsion. This emulsion was subcutaneously injected into a rabbit in ten and several parts. Moreover, the same amount of the protein was mixed with Freund's incomplete adjuvant and the obtained emulsion was subcutaneously injected in the same manner at intervals of 4 weeks. 1 week after the injection, blood was collected from the ear vein and the serum was separated. When the antibody titer was determined by ELISA, an increase in the antibody titer of the serum was observed after the second or third booster. Since a cross reaction with gelsolin was observed, the serum was absorbed by gelsolin immobilized on agarose beads and then absorbed by immobilized adseverin. Next, it was eluted successively with 0.1 M glycine-HCl (pH 2.5), 0.1 M triethylamine-HCl (pH 11.5) and 3.5 M $MgCl_2$, dialyzed against Tris buffer salt solution and concentrated. The affinity purified antibody thus obtained showed no cross reaction with gelsolin but a reaction specific to adseverin. This antibody was used at concentrations of 0.1 to 1 μg/ml in the immunoblotting method and 1 to 10 μg/ml in the fluorescent antibody method.

PREPARATION OF ANTI-PEPTIDE ANTIBODY (ANTIBODY AGAINST HUMAN ADSEVERIN-DERIVED PEPTIDE)

Selection was made of 2 peptide sequences (16 residues) at sites which were exposed on the surface of protein molecules, had been very well conserved beyond difference in species between bovine adseverin and human adseverin and less homologous with gelsolin (SEQ ID NO:8,9). Staring from a resin having a branched structure to which 7 lysine residues were bound, a multiple antigen peptide (MAP) was synthesized (Tam, J. P., Proc. Natl. Acad. Sci. USA 85:5409–5413, 1988). Then emulsions were prepared by using this peptide with Freund's complete adjuvant in the first time and Freund's incomplete adjuvant in the second time and thereafter. These emulsions were subcutaneously injected into 2 rabbits at intervals of 1 week. After 7, 8 and 9 weeks, blood was collected from the ear vein and the antibody titer was determined by ELISA. Thus an antibody, which showed scarcely any cross reaction with gelsolin and reacted with rat, bovine and human adseverins, was obtained. Since a nonspecific reaction shown in the unimmunized serum was observed, affinity purification was carried out similar to the case of the antibody obtained by immunizing with a purified protein.

What is claimed is:

1. An isolated protein comprising an amino acid sequence respresented by SEQ ID NO:7.

2. The isolated protein of claim 1, wherein said protein is a recombinant protein.

* * * * *

UNITED STATES PATENT AND TRADEMARK OFFICE
CERTIFICATE OF CORRECTION

PATENT NO. : 6,184,352 B1  
APPLICATION NO. : 09/469253  
DATED : February 6, 2001  
INVENTOR(S) : Seiji Nakamura et al.

It is certified that error appears in the above-identified patent and that said Letters Patent is hereby corrected as shown below:

On the title page item (75), line 3, change "Juni-ichi Nezu" to -- Jun-ichi Nezu --.

On the title page item (62), line 1, Related U.S. Application Data, change "Division of application No. 08/669,286, filed as application No. PCT/JP94/02227 on Dec. 27, 1994" to -- Division of application No. 08/669,286 filed on June 28, 1996 which is the national phase of PCT International application No. PCT/JP94/02227 filed on December 27, 1994. --

Signed and Sealed this

Twelfth Day of September, 2006

JON W. DUDAS  
*Director of the United States Patent and Trademark Office*

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Lys Val Ala His Val Lys Gln Ile Pro Phe Asp Ala
1               5                   10

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Val Leu Thr Asn Asp Leu Thr Ala Gln
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ile Thr Asn Arg Lys
1               5

(2) INFORMATION FOR SEQ ID NO:4:

(i) SEQUENCE CHARACTERISTICS:
        (A) LENGTH: 2418 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 27..2171

(xi) SEQUENCE DESCRIPTION: SEQ ID NO:4:

```
CGGCCGGAAC ATCGCGTGCC CGAGTC ATG GCC CAG GGG CTG TAC CAC GAG GAG        53
                            Met Ala Gln Gly Leu Tyr His Glu Glu
                              1               5

TTC GCC CGC GCG GGC AAG CGG GCG GGG CTG CAG GTC TGG AGA ATT GAG        101
Phe Ala Arg Ala Gly Lys Arg Ala Gly Leu Gln Val Trp Arg Ile Glu
 10              15                  20                  25

AAG CTG GAG CTG GTG CCG GTG CCC GAG AGC GCG TAT GGC AAC TTC TAC        149
Lys Leu Glu Leu Val Pro Val Pro Glu Ser Ala Tyr Gly Asn Phe Tyr
                 30                  35                  40

GTC GGG GAT GCC TAC CTG GTG CTC CAC ACG ACG CAG GCC AGC CGG GGC        197
Val Gly Asp Ala Tyr Leu Val Leu His Thr Thr Gln Ala Ser Arg Gly
             45                  50                  55

TTC ACC TAC CGC CTG CAC TTC TGG CTG GGA AAG GAG TGT ACT CAG GAT        245
Phe Thr Tyr Arg Leu His Phe Trp Leu Gly Lys Glu Cys Thr Gln Asp
         60                  65                  70

GAA AGC ACA GCA GCT GCC ATC TTT ACT GTT CAG ATG GAT GAC TAT TTG        293
Glu Ser Thr Ala Ala Ala Ile Phe Thr Val Gln Met Asp Asp Tyr Leu
     75                  80                  85

GGT GGC AAA CCT GTG CAG AAC AGA GAA CTT CAA GGC TAT GAG TCT ACG        341
Gly Gly Lys Pro Val Gln Asn Arg Glu Leu Gln Gly Tyr Glu Ser Thr
 90                  95                 100                 105

GAT TTT GTT GGC TAC TTT AAA GGA GGT CTG AAA TAC AAG GCT GGC GGT        389
Asp Phe Val Gly Tyr Phe Lys Gly Gly Leu Lys Tyr Lys Ala Gly Gly
                110                 115                 120

GTG GCG TCT GGA CTC AAT CAT GTG CTT ACA AAT GAC TTG ACT GCT CAG        437
Val Ala Ser Gly Leu Asn His Val Leu Thr Asn Asp Leu Thr Ala Gln
            125                 130                 135

AGG CTC CTG CAT GTG AAA GGT CGG AGA GTC GTC AGG GCC ACG GAA GTT        485
Arg Leu Leu His Val Lys Gly Arg Arg Val Val Arg Ala Thr Glu Val
        140                 145                 150

CCC CTA AGC TGG GAC AGT TTC AAC AAG GGT GAC TGC TTC ATC ATT GAC        533
Pro Leu Ser Trp Asp Ser Phe Asn Lys Gly Asp Cys Phe Ile Ile Asp
    155                 160                 165

CTT GGC ACT GAA ATT TAC CAG TGG TGT GGA TCT TCT TGC AAC AAG TAC        581
Leu Gly Thr Glu Ile Tyr Gln Trp Cys Gly Ser Ser Cys Asn Lys Tyr
```

```
                    -continued 170                 175                 180                 185

GAG CGC CTG AAG GCC AGC CAG GTT GCC ATC GGC ATT CGG GAC AAT GAA       629
Glu Arg Leu Lys Ala Ser Gln Val Ala Ile Gly Ile Arg Asp Asn Glu
                190                 195                 200

AGG AAA GGC AGA GCT CAG CTG ATT GTG GTA GAA GAA GGG AGT GAA CCA       677
Arg Lys Gly Arg Ala Gln Leu Ile Val Val Glu Glu Gly Ser Glu Pro
                205                 210                 215

TCA GAG CTT ACA AAG GTA TTA GGG GAA AAG CCA AAG CTT AGG GAT GGA       725
Ser Glu Leu Thr Lys Val Leu Gly Glu Lys Pro Lys Leu Arg Asp Gly
                220                 225                 230

GAA GAT GAT GAT GAC ATC AAA GCA GAT ATA ACT AAT AGG AAA ATG GCT       773
Glu Asp Asp Asp Asp Ile Lys Ala Asp Ile Thr Asn Arg Lys Met Ala
        235                 240                 245

AAA CTC TAC ATG GTT TCA GAT GCC AGT GGC TCC ATG AAA GTG AGT CTG       821
Lys Leu Tyr Met Val Ser Asp Ala Ser Gly Ser Met Lys Val Ser Leu
250                 255                 260                 265

GTG GCA GAA GAA AAC CCC TTC TCC ATG GCG ATG CTT CTG TCT GAA GAA       869
Val Ala Glu Glu Asn Pro Phe Ser Met Ala Met Leu Leu Ser Glu Glu
                270                 275                 280

TGC TTC ATT TTG GAC CAC GGT GCT GCA AAA CAG ATT TTT GTA TGG AAA       917
Cys Phe Ile Leu Asp His Gly Ala Ala Lys Gln Ile Phe Val Trp Lys
                285                 290                 295

GGT AAA GAT GCT AAT CCC CAG GAG AGA AAG GCT GCC ATG AAG ACA GCT       965
Gly Lys Asp Ala Asn Pro Gln Glu Arg Lys Ala Ala Met Lys Thr Ala
                300                 305                 310

GAG GAA TTC CTA CAG CAA ATG AAT TAT TCT ACG AAT ACC CAA ATT CAA      1013
Glu Glu Phe Leu Gln Gln Met Asn Tyr Ser Thr Asn Thr Gln Ile Gln
        315                 320                 325

GTT CTT CCA GAA GGA GGT GAA ACA CCA ATC TTC AAA CAG TTC TTT AAG      1061
Val Leu Pro Glu Gly Gly Glu Thr Pro Ile Phe Lys Gln Phe Phe Lys
330                 335                 340                 345

GAC TGG AGA GAT AGA GAT CAG AGC GAT GGC TTC GGG AAA GTG TAT GTC      1109
Asp Trp Arg Asp Arg Asp Gln Ser Asp Gly Phe Gly Lys Val Tyr Val
                350                 355                 360

ACA GAA AAA GTG GCT CAC GTA AAA CAA ATT CCA TTT GAT GCC TCA AAA      1157
Thr Glu Lys Val Ala His Val Lys Gln Ile Pro Phe Asp Ala Ser Lys
                365                 370                 375

TTG CAC AGC TCC CCA CAA ATG GCA GCC CAG CAT CAC GTG GTG GAT GAC      1205
Leu His Ser Ser Pro Gln Met Ala Ala Gln His His Val Val Asp Asp
                380                 385                 390

GGT TCT GGC AAA GTG CAG ATT TGG CGT GTA GAA AAC AAC GGT AGG GTC      1253
Gly Ser Gly Lys Val Gln Ile Trp Arg Val Glu Asn Asn Gly Arg Val
        395                 400                 405

GAA ATT GAC CGA AAC TCG TAT GGT GAA TTC TAT GGT GGT GAT TGC TAC      1301
Glu Ile Asp Arg Asn Ser Tyr Gly Glu Phe Tyr Gly Gly Asp Cys Tyr
410                 415                 420                 425

ATT ATA CTT TAC ACT TAT CCC AGA GGA CAG ATT ATC TAC ACC TGG CAA      1349
Ile Ile Leu Tyr Thr Tyr Pro Arg Gly Gln Ile Ile Tyr Thr Trp Gln
                430                 435                 440

GGA GCA AAT GCC ACA CGG GAT GAG CTG ACA ACC TCC GCA TTC CTG ACT      1397
Gly Ala Asn Ala Thr Arg Asp Glu Leu Thr Thr Ser Ala Phe Leu Thr
                445                 450                 455

GTT CAG TTG GAT AGA TCC CTC GGG GGA CAG GCT GTG CAG ATT CGA GTC      1445
Val Gln Leu Asp Arg Ser Leu Gly Gly Gln Ala Val Gln Ile Arg Val
                460                 465                 470

TCC CAA GGC AAA GAA CCT GCT CAC CTG CTG AGT TTG TTC AAA GAC AAA      1493
Ser Gln Gly Lys Glu Pro Ala His Leu Leu Ser Leu Phe Lys Asp Lys
        475                 480                 485

CCG CTC ATT ATT TAC AAG AAC GGA ACA TCA AAG AAA GAA GGT CAG GCA      1541
```

```
Pro Leu Ile Ile Tyr Lys Asn Gly Thr Ser Lys Lys Glu Gly Gln Ala
490                 495                 500                 505

CCA GCC CCC CCT ATA CGC CTC TTT CAA GTC CGA AGA AAC CTG GCT TCG      1589
Pro Ala Pro Pro Ile Arg Leu Phe Gln Val Arg Arg Asn Leu Ala Ser
                510                 515                 520

ATC ACC AGA ATT ATG GAG GTA GAT GTT GAT GCA AAC TCA TTG AAT TCC      1637
Ile Thr Arg Ile Met Glu Val Asp Val Asp Ala Asn Ser Leu Asn Ser
                525                 530                 535

AAT GAT GTT TTT GTC CTG AAA CTG CGA CAA AAT AAT GGC TAC ATC TGG      1685
Asn Asp Val Phe Val Leu Lys Leu Arg Gln Asn Asn Gly Tyr Ile Trp
                540                 545                 550

ATA GGA AAA GGC TCC ACA CAG GAG GAG GAG AAA GGA GCA GAG TAC GTG      1733
Ile Gly Lys Gly Ser Thr Gln Glu Glu Glu Lys Gly Ala Glu Tyr Val
555                 560                 565

GCA AGC GTC CTC AAA TGC AAA ACT TCG ACG ATT CAG GAA GGC AAG GAA      1781
Ala Ser Val Leu Lys Cys Lys Thr Ser Thr Ile Gln Glu Gly Lys Glu
570                 575                 580                 585

CCA GAG GAG TTT TGG AAT TCC CTT GGA GGG AAA AAA GAC TAC CAG ACC      1829
Pro Glu Glu Phe Trp Asn Ser Leu Gly Gly Lys Lys Asp Tyr Gln Thr
                590                 595                 600

TCT CCT CTG CTA GAA TCC CAG GCT GAA GAC CAT CCA CCT CGG CTT TAC      1877
Ser Pro Leu Leu Glu Ser Gln Ala Glu Asp His Pro Pro Arg Leu Tyr
                605                 610                 615

GGC TGC TCC AAC AAA ACT GGA AGA TTC ATT ATT GAA GAG GTT CCA GGA      1925
Gly Cys Ser Asn Lys Thr Gly Arg Phe Ile Ile Glu Glu Val Pro Gly
                620                 625                 630

GAG TTC ACC CAG GAT GAT TTA GCA GAA GAT GAT GTC ATG CTG TTA GAT      1973
Glu Phe Thr Gln Asp Asp Leu Ala Glu Asp Asp Val Met Leu Leu Asp
635                 640                 645

GCT TGG GAA CAG ATT TTT ATT TGG ATT GGA AAA GAT GCC AAT GAA GTT      2021
Ala Trp Glu Gln Ile Phe Ile Trp Ile Gly Lys Asp Ala Asn Glu Val
650                 655                 660                 665

GAG AAA TCA GAA TCT CTG AAG TCT GCC AAA ATA TAC CTT GAG ACC GAC      2069
Glu Lys Ser Glu Ser Leu Lys Ser Ala Lys Ile Tyr Leu Glu Thr Asp
                670                 675                 680

CCT TCT GGA AGA GAC AAG AGG ACG CCA ATT GTC ATC ATA AAA CAG GGT      2117
Pro Ser Gly Arg Asp Lys Arg Thr Pro Ile Val Ile Ile Lys Gln Gly
                685                 690                 695

CAT GAG CCA CCT ACT TTC ACA GGC TGG TTC CTG GGC TGG GAT TCC AGC      2165
His Glu Pro Pro Thr Phe Thr Gly Trp Phe Leu Gly Trp Asp Ser Ser
                700                 705                 710

AGG TGG TAAACTGATT TTTGTAGGAA AAAAACAAAT ATAATGGGGC AGCTGTCCCA       2221
Arg Trp
    715

GGGGGGAAGG AGGAGCTTGT TTAACTTTAG AAAATTAACC TCAGCCATAT GGCTATTTTT    2281

CCGTGCTTAG AATTGGTTTG AAATTTCTTT TAAACTGGAA TTTTCTTATG TTAATATTTT    2341

TATAACTTTT CTTATGGACC AATATTAGCT CTGCTGGATG CTGACATATC TTTATATATG    2401

ACTTTTTAAA GGGGCCG                                                   2418

(2) INFORMATION FOR SEQ ID NO:5:

(i) SEQUENCE CHARACTERISTICS:
        (A) LENGTH: 715 amino acids
        (B) TYPE: amino acid
        (D) TOPOLOGY: linear (ii) MOLECULE TYPE: protein (xi) SEQUENCE DESCRIPTION: SEQ ID NO:5:
```

-continued

```
Met Ala Gln Gly Leu Tyr His Glu Glu Phe Ala Arg Ala Gly Lys Arg
 1               5                  10                  15

Ala Gly Leu Gln Val Trp Arg Ile Glu Lys Leu Glu Leu Val Pro Val
            20                  25                  30

Pro Glu Ser Ala Tyr Gly Asn Phe Tyr Val Gly Asp Ala Tyr Leu Val
            35                  40                  45

Leu His Thr Thr Gln Ala Ser Arg Gly Phe Thr Tyr Arg Leu His Phe
    50                  55                  60

Trp Leu Gly Lys Glu Cys Thr Gln Asp Glu Ser Thr Ala Ala Ala Ile
65                  70                  75                  80

Phe Thr Val Gln Met Asp Asp Tyr Leu Gly Lys Pro Val Gln Asn
                85                  90                  95

Arg Glu Leu Gln Gly Tyr Glu Ser Thr Asp Phe Val Gly Tyr Phe Lys
            100                 105                 110

Gly Gly Leu Lys Tyr Lys Ala Gly Gly Val Ala Ser Gly Leu Asn His
            115                 120                 125

Val Leu Thr Asn Asp Leu Thr Ala Gln Arg Leu Leu His Val Lys Gly
    130                 135                 140

Arg Arg Val Val Arg Ala Thr Glu Val Pro Leu Ser Trp Asp Ser Phe
145                 150                 155                 160

Asn Lys Gly Asp Cys Phe Ile Ile Asp Leu Gly Thr Glu Ile Tyr Gln
                165                 170                 175

Trp Cys Gly Ser Ser Cys Asn Lys Tyr Glu Arg Leu Lys Ala Ser Gln
            180                 185                 190

Val Ala Ile Gly Ile Arg Asp Asn Glu Arg Lys Gly Arg Ala Gln Leu
            195                 200                 205

Ile Val Val Glu Glu Gly Ser Glu Pro Ser Glu Leu Thr Lys Val Leu
    210                 215                 220

Gly Glu Lys Pro Lys Leu Arg Asp Gly Glu Asp Asp Asp Ile Lys
225                 230                 235                 240

Ala Asp Ile Thr Asn Arg Lys Met Ala Lys Leu Tyr Met Val Ser Asp
                245                 250                 255

Ala Ser Gly Ser Met Lys Val Ser Leu Val Ala Glu Glu Asn Pro Phe
            260                 265                 270

Ser Met Ala Met Leu Leu Ser Glu Glu Cys Phe Ile Leu Asp His Gly
    275                 280                 285

Ala Ala Lys Gln Ile Phe Val Trp Lys Gly Lys Asp Ala Asn Pro Gln
    290                 295                 300

Glu Arg Lys Ala Ala Met Lys Thr Ala Glu Glu Phe Leu Gln Gln Met
305                 310                 315                 320

Asn Tyr Ser Thr Asn Thr Gln Ile Gln Val Leu Pro Glu Gly Gly Glu
                325                 330                 335

Thr Pro Ile Phe Lys Gln Phe Lys Asp Trp Arg Asp Arg Asp Gln
            340                 345                 350

Ser Asp Gly Phe Gly Lys Val Tyr Val Thr Glu Lys Val Ala His Val
            355                 360                 365

Lys Gln Ile Pro Phe Asp Ala Ser Lys Leu His Ser Ser Pro Gln Met
    370                 375                 380

Ala Ala Gln His His Val Val Asp Asp Gly Ser Gly Lys Val Gln Ile
385                 390                 395                 400

Trp Arg Val Glu Asn Asn Gly Arg Val Glu Ile Asp Arg Asn Ser Tyr
                405                 410                 415

Gly Glu Phe Tyr Gly Gly Asp Cys Tyr Ile Ile Leu Tyr Thr Tyr Pro
```

|  | | | | | 420 | | | | | 425 | | | | | 430 | |
|---|---|---|---|---|---|---|---|---|---|---|---|---|---|---|---|---|

Arg Gly Gln Ile Ile Tyr Thr Trp Gln Gly Ala Asn Ala Thr Arg Asp
           435                        440                      445

Glu Leu Thr Thr Ser Ala Phe Leu Thr Val Gln Leu Asp Arg Ser Leu
    450                        455                      460

Gly Gly Gln Ala Val Gln Ile Arg Val Ser Gln Gly Lys Glu Pro Ala
465                 470                      475                      480

His Leu Leu Ser Leu Phe Lys Asp Lys Pro Leu Ile Ile Tyr Lys Asn
           485                        490                      495

Gly Thr Ser Lys Lys Glu Gly Gln Ala Pro Ala Pro Pro Ile Arg Leu
        500                      505                      510

Phe Gln Val Arg Arg Asn Leu Ala Ser Ile Thr Arg Ile Met Glu Val
    515                        520                      525

Asp Val Asp Ala Asn Ser Leu Asn Ser Asn Asp Val Phe Val Leu Lys
           530                        535                      540

Leu Arg Gln Asn Asn Gly Tyr Ile Trp Ile Gly Lys Gly Ser Thr Gln
545                 550                      555                      560

Glu Glu Glu Lys Gly Ala Glu Tyr Val Ala Ser Val Leu Lys Cys Lys
           565                        570                      575

Thr Ser Thr Ile Gln Glu Gly Lys Glu Pro Glu Glu Phe Trp Asn Ser
        580                      585                      590

Leu Gly Gly Lys Lys Asp Tyr Gln Thr Ser Pro Leu Leu Glu Ser Gln
    595                        600                      605

Ala Glu Asp His Pro Pro Arg Leu Tyr Gly Cys Ser Asn Lys Thr Gly
           610                        615                      620

Arg Phe Ile Ile Glu Glu Val Pro Gly Glu Phe Thr Gln Asp Asp Leu
625                 630                      635                      640

Ala Glu Asp Asp Val Met Leu Leu Asp Ala Trp Glu Gln Ile Phe Ile
           645                        650                      655

Trp Ile Gly Lys Asp Ala Asn Glu Val Glu Lys Ser Glu Ser Leu Lys
        660                      665                      670

Ser Ala Lys Ile Tyr Leu Glu Thr Asp Pro Ser Gly Arg Asp Lys Arg
    675                        680                      685

Thr Pro Ile Val Ile Ile Lys Gln Gly His Glu Pro Pro Thr Phe Thr
           690                        695                      700

Gly Trp Phe Leu Gly Trp Asp Ser Ser Arg Trp
705                 710                      715

(2) INFORMATION FOR SEQ ID NO:6:

(i) SEQUENCE CHARACTERISTICS:
        (A) LENGTH: 2630 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 79..2223

(xi) SEQUENCE DESCRIPTION: SEQ ID NO:6:

AAGGTTCCTC CTGCTGCTCT CGGTTTAGTC CAAGATCAGC GATATCACGC GTCCCCCGGA      60

GCATCGCGTG CAGGAGCC ATG GCG CGG GAG CTA TAC CAC GAA GAG TTC GCC     111
                           Met Ala Arg Glu Leu Tyr His Glu Glu Phe Ala
                            1                5                    10

```
CGG GCG GGC AAG CAG GCG GGG CTG CAG GTC TGG AGG ATT GAG AAG CTG       159
Arg Ala Gly Lys Gln Ala Gly Leu Gln Val Trp Arg Ile Glu Lys Leu
            15                  20                  25

GAG CTG GTG CCC GTG CCC CAG AGC GCT CAC GGC GAC TTC TAC GTC GGG       207
Glu Leu Val Pro Val Pro Gln Ser Ala His Gly Asp Phe Tyr Val Gly
        30                  35                  40

GAT GCC TAC CTG GTG CTG CAC ACG GCC AAG ACG AGC CGA GGC TTC ACC       255
Asp Ala Tyr Leu Val Leu His Thr Ala Lys Thr Ser Arg Gly Phe Thr
    45                  50                  55

TAC CAC CTG CAC TTC TGG CTC GGA AAG GAG TGT TCC CAG GAT GAA AGC       303
Tyr His Leu His Phe Trp Leu Gly Lys Glu Cys Ser Gln Asp Glu Ser
60                  65                  70                  75

ACA GCT GCT GCC ATC TTC ACT GTT CAG ATG GAT GAC TAT TTG GGT GGC       351
Thr Ala Ala Ala Ile Phe Thr Val Gln Met Asp Asp Tyr Leu Gly Gly
                80                  85                  90

AAG CCA GTG CAG AAT AGA GAA CTT CAA GGA TAT GAG TCT AAT GAC TTT       399
Lys Pro Val Gln Asn Arg Glu Leu Gln Gly Tyr Glu Ser Asn Asp Phe
            95                 100                 105

GTT AGC TAT TTC AAA GGC GGT CTG AAA TAC AAG GCT GGA GGC GTG GCA       447
Val Ser Tyr Phe Lys Gly Gly Leu Lys Tyr Lys Ala Gly Gly Val Ala
        110                 115                 120

TCT GGA TTA AAT CAT GTT CTT ACG AAC GAC CTG ACA GCC AAG AGG CTC       495
Ser Gly Leu Asn His Val Leu Thr Asn Asp Leu Thr Ala Lys Arg Leu
    125                 130                 135

CTA CAT GTG AAG GGT CGT AGA GTG GTG AGA GCC ACA GAA GTT CCC CTT       543
Leu His Val Lys Gly Arg Arg Val Val Arg Ala Thr Glu Val Pro Leu
140                 145                 150                 155

AGC TGG GAC AGT TTC AAC AAG GGT GAC TGC TTC ATC ATT GAC CTT GGC       591
Ser Trp Asp Ser Phe Asn Lys Gly Asp Cys Phe Ile Ile Asp Leu Gly
                160                 165                 170

ACC GAA ATT TAT CAG TGG TGT GGT TCC TCG TGC AAC AAA TAT GAA CGT       639
Thr Glu Ile Tyr Gln Trp Cys Gly Ser Ser Cys Asn Lys Tyr Glu Arg
            175                 180                 185

CTG AAG GCA AAC CAG GTA GCT ACT GGC ATT CGG TAC AAT GAA AGG AAA       687
Leu Lys Ala Asn Gln Val Ala Thr Gly Ile Arg Tyr Asn Glu Arg Lys
        190                 195                 200

GGA AGG TCT GAA CTA ATT GTC GTG GAA GAA GGA AGT GAA CCC TCA GAA       735
Gly Arg Ser Glu Leu Ile Val Val Glu Glu Gly Ser Glu Pro Ser Glu
    205                 210                 215

CTT ATA AAG GTC TTA GGG GAA AAG CCA GAG CTT CCA GAT GGA GGT GAT       783
Leu Ile Lys Val Leu Gly Glu Lys Pro Glu Leu Pro Asp Gly Gly Asp
220                 225                 230                 235

GAT GAT GAC ATT ATA GCA GAC ATA AGT AAC AGG AAA ATG GCT AAA CTA       831
Asp Asp Asp Ile Ile Ala Asp Ile Ser Asn Arg Lys Met Ala Lys Leu
                240                 245                 250

TAC ATG GTT TCA GAT GCA AGT GGC TCC ATG AGA GTG ACT GTG GTG GCA       879
Tyr Met Val Ser Asp Ala Ser Gly Ser Met Arg Val Thr Val Val Ala
            255                 260                 265

GAA GAA AAC CCC TTC TCA ATG GCA ATG CTG CTG TCT GAA GAA TGC TTT       927
Glu Glu Asn Pro Phe Ser Met Ala Met Leu Leu Ser Glu Glu Cys Phe
        270                 275                 280

ATT TTG GAC CAC GGG GCT GCC AAA CAA ATT TTC GTA TGG AAA GGT AAA       975
Ile Leu Asp His Gly Ala Ala Lys Gln Ile Phe Val Trp Lys Gly Lys
    285                 290                 295

GAT GCT AAT CCC CAA GAG AGG AAG GCT GCA ATG AAG ACA GCT GAA GAA      1023
Asp Ala Asn Pro Gln Glu Arg Lys Ala Ala Met Lys Thr Ala Glu Glu
300                 305                 310                 315

TTT CTA CAG CAA ATG AAT TAT TCC AAG AAT ACC CAA ATT CAA GTT CTT      1071
Phe Leu Gln Gln Met Asn Tyr Ser Lys Asn Thr Gln Ile Gln Val Leu
                320                 325                 330
```

```
CCA GAA GGA GGT GAA ACA CCA ATC TTC AAA CAG TTT TTT AAG GAC TGG      1119
Pro Glu Gly Gly Glu Thr Pro Ile Phe Lys Gln Phe Phe Lys Asp Trp
            335                 340                 345

AGA GAT AAA GAT CAG AGT GAT GGC TTC GGG AAA GTT TAT GTC ACA GAG      1167
Arg Asp Lys Asp Gln Ser Asp Gly Phe Gly Lys Val Tyr Val Thr Glu
            350                 355                 360

AAA GTG GCT CAA ATA AAA CAA ATT CCC TTT GAT GCC TCA AAA TTA CAC      1215
Lys Val Ala Gln Ile Lys Gln Ile Pro Phe Asp Ala Ser Lys Leu His
365                 370                 375

AGT TCT CCG CAG ATG GCA GCC CAG CAC AAT ATG GTG GAT GAT GGT TCT      1263
Ser Ser Pro Gln Met Ala Ala Gln His Asn Met Val Asp Asp Gly Ser
380                 385                 390                 395

GGC AAA GTG GAG ATT TGG CGT GTA GAA AAC AAT GGT AGG ATC CAA GTT      1311
Gly Lys Val Glu Ile Trp Arg Val Glu Asn Asn Gly Arg Ile Gln Val
                400                 405                 410

GAC CAA AAC TCA TAT GGT GAA TTC TAT GGT GGT GAC TGC TAC ATC ATA      1359
Asp Gln Asn Ser Tyr Gly Glu Phe Tyr Gly Gly Asp Cys Tyr Ile Ile
            415                 420                 425

CTC TAC ACC TAT CCC AGA GGA CAG ATT ATC TAC ACG TGG CAA GGA GCA      1407
Leu Tyr Thr Tyr Pro Arg Gly Gln Ile Ile Tyr Thr Trp Gln Gly Ala
            430                 435                 440

AAT GCC ACA CGA GAT GAG CTG ACA ACA TCT GCG TTC CTG ACT GTT CAG      1455
Asn Ala Thr Arg Asp Glu Leu Thr Thr Ser Ala Phe Leu Thr Val Gln
    445                 450                 455

TTG GAT CGG TCC CTT GGA GGA CAG GCT GTG CAG ATC CGA GTC TCC CAA      1503
Leu Asp Arg Ser Leu Gly Gly Gln Ala Val Gln Ile Arg Val Ser Gln
460                 465                 470                 475

GGC AAA GAG CCT GTT CAC CTA CTG AGT TTG TTC AAA GAC AAA CCG CTC      1551
Gly Lys Glu Pro Val His Leu Leu Ser Leu Phe Lys Asp Lys Pro Leu
                480                 485                 490

ATT ATT TAC AAG AAT GGA ACA TCA AAG AAA GGA GGT CAG GCA CCT GCT      1599
Ile Ile Tyr Lys Asn Gly Thr Ser Lys Lys Gly Gly Gln Ala Pro Ala
            495                 500                 505

CCC CCT ACA CGC CTC TTT CAA GTC CGG AGA AAC CTG GCA TCT ATC ACC      1647
Pro Pro Thr Arg Leu Phe Gln Val Arg Arg Asn Leu Ala Ser Ile Thr
            510                 515                 520

AGA ATT GTG GAG GTT GAT GTT GAT GCA AAT TCA CTG AAT TCT AAC GAT      1695
Arg Ile Val Glu Val Asp Val Asp Ala Asn Ser Leu Asn Ser Asn Asp
525                 530                 535

GTT TGT GTC CTG AAA CTG CCA CAA AAT AGT GGC TAC ATC TGG GTA GGA      1743
Val Cys Val Leu Lys Leu Pro Gln Asn Ser Gly Tyr Ile Trp Val Gly
540                 545                 550                 555

AAA GGT GCT AGC CAG GAG GAG GAG AAA GGA GCA GAG TAT GTA GCA AGT      1791
Lys Gly Ala Ser Gln Glu Glu Glu Lys Gly Ala Glu Tyr Val Ala Ser
                560                 565                 570

GTC CTA AAG TGC AAA ACC TTA AGG ATC CAA GAA GGC GAG GAG CCA GAG      1839
Val Leu Lys Cys Lys Thr Leu Arg Ile Gln Glu Gly Glu Glu Pro Glu
            575                 580                 585

GAG TTC TGG AAT TCC CTT GGA GGG AAA AAA GAC TAC CAG ACC TCA CCA      1887
Glu Phe Trp Asn Ser Leu Gly Gly Lys Lys Asp Tyr Gln Thr Ser Pro
            590                 595                 600

CTA CTG GAA ACC CAG GCT GAA GAC CAT CCA CCT CGG CTT TAC GGC TGC      1935
Leu Leu Glu Thr Gln Ala Glu Asp His Pro Pro Arg Leu Tyr Gly Cys
605                 610                 615

TCT AAC AAA ACT GGA AGA TTT GTT ATT GAA GAG ATT CCA GGA GAG TTC      1983
Ser Asn Lys Thr Gly Arg Phe Val Ile Glu Glu Ile Pro Gly Glu Phe
620                 625                 630                 635

ACC CAG GAT GAT TTA GCT GAA GAT GAT GTC ATG TTA CTA GAT GCT TGG      2031
Thr Gln Asp Asp Leu Ala Glu Asp Asp Val Met Leu Leu Asp Ala Trp
```

-continued

```
                    640                 645                 650
GAA CAG ATA TTT ATT TGG ATT GGC AAA GAT GCT AAT GAA GTT GAG AAA    2079
Glu Gln Ile Phe Ile Trp Ile Gly Lys Asp Ala Asn Glu Val Glu Lys
                655                 660                 665

AAA GAA TCT CTG AAG TCT GCC AAA ATG TAC CTT GAG ACA GAC CCT TCT    2127
Lys Glu Ser Leu Lys Ser Ala Lys Met Tyr Leu Glu Thr Asp Pro Ser
                670                 675                 680

GGA AGA GAC AAG AGG ACA CCA ATT GTC ATC ATA AAA CAG GGC CAT GAG    2175
Gly Arg Asp Lys Arg Thr Pro Ile Val Ile Ile Lys Gln Gly His Glu
                685                 690                 695

CCA CCC ACA TTC ACA GGC TGG TTC CTG GGC TGG GAT TCC AGC AAG TGG    2223
Pro Pro Thr Phe Thr Gly Trp Phe Leu Gly Trp Asp Ser Ser Lys Trp
700                 705                 710                 715

TAAATTGGTA TTTGTAAAAA GCAAACAAAC ATTACAAGGC AGTTATCTCA TTGCTGTTTT    2283

GGGAGAGGAA CGGGAAAAGC TTTTTGCTTA TTTGTCTTTT GAAAATTAAG GCTGGGCGCG    2343

GTGGCTCACA CCTGTAATCC CAGCACTTTG AGAGGATGAG GTAGGCGGAT CACTGGGGTC    2403

AGGATTTCGA GACCAGCCTG GCCAACATGG CGAAACCTCG CCTCTACTAA AAATACAAAA    2463

AAATTAGCTG CGCGTGGTGG TGCACGCCTG TAGTCCCTGC TACTTGGAAG GCTGAGACAG    2523

GAAAATTGCT TGAGCCCAGG AGGCTGAGGT TGCAGTGAGC CAGGATTGCG CCACCACACT    2583

CCAGCCTGGG CAACAGAGAC TCTGTCTCAA AAAAAAAAAA AAAAAA                   2630
```

(2) INFORMATION FOR SEQ ID NO:7:

(i) SEQUENCE CHARACTERISTICS:
        (A) LENGTH: 715 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ala Arg Glu Leu Tyr His Glu Glu Phe Ala Arg Ala Gly Lys Gln
 1               5                  10                  15

Ala Gly Leu Gln Val Trp Arg Ile Glu Lys Leu Glu Leu Val Pro Val
                20                  25                  30

Pro Gln Ser Ala His Gly Asp Phe Tyr Val Gly Asp Ala Tyr Leu Val
            35                  40                  45

Leu His Thr Ala Lys Thr Ser Arg Gly Phe Thr Tyr His Leu His Phe
        50                  55                  60

Trp Leu Gly Lys Glu Cys Ser Gln Asp Glu Ser Thr Ala Ala Ala Ile
 65                  70                  75                  80

Phe Thr Val Gln Met Asp Asp Tyr Leu Gly Gly Lys Pro Val Gln Asn
                85                  90                  95

Arg Glu Leu Gln Gly Tyr Glu Ser Asn Asp Phe Val Ser Tyr Phe Lys
                100                 105                 110

Gly Gly Leu Lys Tyr Lys Ala Gly Gly Val Ala Ser Gly Leu Asn His
            115                 120                 125

Val Leu Thr Asn Asp Leu Thr Ala Lys Arg Leu His Val Lys Gly
        130                 135                 140

Arg Arg Val Val Arg Ala Thr Glu Val Pro Leu Ser Trp Asp Ser Phe
145                 150                 155                 160

Asn Lys Gly Asp Cys Phe Ile Ile Asp Leu Gly Thr Glu Ile Tyr Gln
                165                 170                 175

Trp Cys Gly Ser Ser Cys Asn Lys Tyr Glu Arg Leu Lys Ala Asn Gln
                180                 185                 190
```

-continued

```
Val Ala Thr Gly Ile Arg Tyr Asn Glu Arg Lys Gly Arg Ser Glu Leu
        195                 200                 205

Ile Val Val Glu Glu Gly Ser Glu Pro Ser Glu Leu Ile Lys Val Leu
        210                 215                 220

Gly Glu Lys Pro Glu Leu Pro Asp Gly Gly Asp Asp Asp Ile Ile
225                 230                 235                 240

Ala Asp Ile Ser Asn Arg Lys Met Ala Lys Leu Tyr Met Val Ser Asp
                245                 250                 255

Ala Ser Gly Ser Met Arg Val Thr Val Val Ala Glu Glu Asn Pro Phe
                260                 265                 270

Ser Met Ala Met Leu Leu Ser Glu Glu Cys Phe Ile Leu Asp His Gly
        275                 280                 285

Ala Ala Lys Gln Ile Phe Val Trp Lys Gly Lys Asp Ala Asn Pro Gln
        290                 295                 300

Glu Arg Lys Ala Ala Met Lys Thr Ala Glu Glu Phe Leu Gln Gln Met
305                 310                 315                 320

Asn Tyr Ser Lys Asn Thr Gln Ile Gln Val Leu Pro Glu Gly Gly Glu
                325                 330                 335

Thr Pro Ile Phe Lys Gln Phe Phe Lys Asp Trp Arg Asp Lys Asp Gln
                340                 345                 350

Ser Asp Gly Phe Gly Lys Val Tyr Val Thr Glu Lys Val Ala Gln Ile
        355                 360                 365

Lys Gln Ile Pro Phe Asp Ala Ser Lys Leu His Ser Ser Pro Gln Met
        370                 375                 380

Ala Ala Gln His Asn Met Val Asp Asp Gly Ser Gly Lys Val Glu Ile
385                 390                 395                 400

Trp Arg Val Glu Asn Asn Gly Arg Ile Gln Val Asp Gln Asn Ser Tyr
                405                 410                 415

Gly Glu Phe Tyr Gly Gly Asp Cys Tyr Ile Ile Leu Tyr Thr Tyr Pro
                420                 425                 430

Arg Gly Gln Ile Ile Tyr Thr Trp Gln Gly Ala Asn Ala Thr Arg Asp
        435                 440                 445

Glu Leu Thr Thr Ser Ala Phe Leu Thr Val Gln Leu Asp Arg Ser Leu
        450                 455                 460

Gly Gly Gln Ala Val Gln Ile Arg Val Ser Gln Gly Lys Glu Pro Val
465                 470                 475                 480

His Leu Leu Ser Leu Phe Lys Asp Lys Pro Leu Ile Ile Tyr Lys Asn
                485                 490                 495

Gly Thr Ser Lys Lys Gly Gly Gln Ala Pro Ala Pro Pro Thr Arg Leu
                500                 505                 510

Phe Gln Val Arg Arg Asn Leu Ala Ser Ile Thr Arg Ile Val Glu Val
        515                 520                 525

Asp Val Asp Ala Asn Ser Leu Asn Ser Asn Asp Val Cys Val Leu Lys
        530                 535                 540

Leu Pro Gln Asn Ser Gly Tyr Ile Trp Val Gly Lys Gly Ala Ser Gln
545                 550                 555                 560

Glu Glu Glu Lys Gly Ala Glu Tyr Val Ala Ser Val Leu Lys Cys Lys
                565                 570                 575

Thr Leu Arg Ile Gln Glu Gly Glu Glu Pro Glu Glu Phe Trp Asn Ser
                580                 585                 590

Leu Gly Gly Lys Lys Asp Tyr Gln Thr Ser Pro Leu Leu Glu Thr Gln
        595                 600                 605
```

```
Ala Glu Asp His Pro Pro Arg Leu Tyr Gly Cys Ser Asn Lys Thr Gly
    610                 615                 620

Arg Phe Val Ile Glu Ile Pro Gly Glu Phe Thr Gln Asp Asp Leu
625                 630                 635                 640

Ala Glu Asp Asp Val Met Leu Leu Asp Ala Trp Glu Gln Ile Phe Ile
                    645                 650                 655

Trp Ile Gly Lys Asp Ala Asn Glu Val Glu Lys Glu Ser Leu Lys
                660                 665                 670

Ser Ala Lys Met Tyr Leu Glu Thr Asp Pro Ser Gly Arg Asp Lys Arg
            675                 680                 685

Thr Pro Ile Val Ile Ile Lys Gln Gly His Glu Pro Pro Thr Phe Thr
        690                 695                 700

Gly Trp Phe Leu Gly Trp Asp Ser Ser Lys Trp
705                 710                 715
```

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Leu Asn His Val Leu Thr Asn Asp Leu Thr Ala Lys Arg Leu Leu His
1               5                   10                  15
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Lys Val Tyr Val Thr Glu Lys Val Ala Gln Ile Lys Gln Ile Pro Phe
1               5                   10                  15
```

(2) INFORMATION FOR SEQ ID NO:10:

(i) SEQUENCE CHARACTERISTICS:
        (A) LENGTH: 782 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
                20                  25                  30

Gly Ala Ser Gln Ala Gly Ala Pro Gln Gly Arg Val Pro Glu Ala Arg
            35                  40                  45

Pro Asn Ser Met Val Val Glu His Pro Glu Phe Leu Lys Ala Gly Lys
        50                  55                  60

Glu Pro Gly Leu Gln Ile Trp Arg Val Glu Lys Phe Asp Leu Val Pro
```

-continued

```
              65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
                100                 105                 110

His Tyr Trp Leu Gly Asn Glu Cys Ser Gln Asp Glu Ser Gly Ala Ala
                115                 120                 125

Ala Ile Phe Thr Val Gln Leu Asp Asp Tyr Leu Asn Gly Arg Ala Val
                130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Val Ala Ser Gly Phe
                165                 170                 175

Lys His Val Val Pro Asn Glu Val Val Val Gln Arg Leu Phe Gln Val
                180                 185                 190

Lys Gly Arg Arg Val Val Arg Ala Thr Glu Val Pro Val Ser Trp Glu
                195                 200                 205

Ser Phe Asn Asn Gly Asp Cys Phe Ile Leu Asp Leu Gly Asn Asn Ile
210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
                260                 265                 270

Val Leu Gly Pro Lys Pro Ala Leu Pro Ala Gly Thr Glu Asp Thr Ala
                275                 280                 285

Lys Glu Asp Ala Ala Asn Arg Lys Leu Ala Lys Leu Tyr Lys Val Ser
290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
                340                 345                 350

Glu Glu Arg Lys Ala Ala Leu Lys Thr Ala Ser Asp Phe Ile Thr Lys
                355                 360                 365

Met Asp Tyr Pro Lys Gln Thr Gln Val Ser Val Leu Pro Glu Gly Gly
                370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
                420                 425                 430

Met Ala Ala Gln His Gly Met Asp Asp Asp Gly Thr Gly Gln Lys Gln
                435                 440                 445

Ile Trp Arg Ile Glu Gly Ser Asn Lys Val Pro Val Asp Pro Ala Thr
                450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495
```

-continued

```
Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
            515                 520                 525

Gly Lys Glu Pro Ala His Leu Met Ser Leu Phe Gly Lys Pro Met
        530                 535                 540

Ile Ile Tyr Lys Gly Gly Thr Ser Arg Glu Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
            595                 600                 605

Gly Ala Ser Glu Ala Glu Lys Thr Gly Ala Gln Glu Leu Leu Arg Val
            610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
            675                 680                 685

Met Gln Glu Asp Leu Ala Thr Asp Asp Val Met Leu Leu Asp Thr Trp
        690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
            755                 760                 765

Ser Val Asp Pro Leu Asp Arg Ala Met Ala Glu Leu Ala Ala
        770                 775                 780
```

(2) INFORMATION FOR SEQ ID NO:11:

(i) SEQUENCE CHARACTERISTICS:
        (A) LENGTH: 827 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Met Thr Lys Leu Ser Ala Gln Val Lys Gly Ser Leu Asn Ile Thr Thr
1               5                   10                  15

Pro Gly Leu Gln Ile Trp Arg Ile Glu Ala Met Gln Met Val Pro Val
            20                  25                  30

Pro Ser Ser Thr Phe Gly Ser Phe Asp Gly Asp Cys Tyr Ile Ile
        35                  40                  45

Leu Ala Ile His Lys Thr Ala Ser Ser Leu Ser Tyr Asp Ile His Tyr
    50                  55                  60
```

-continued

```
Trp Ile Gly Gln Asp Ser Ser Leu Asp Glu Gln Gly Ala Ala Ala Ile
 65                  70                  75                  80

Tyr Thr Thr Gln Met Asp Asp Phe Leu Lys Gly Arg Ala Val Gln His
                 85                  90                  95

Arg Glu Val Gln Gly Asn Glu Ser Glu Ala Phe Arg Gly Tyr Phe Lys
            100                 105                 110

Gln Gly Leu Val Ile Arg Lys Gly Val Ala Ser Gly Met Lys His
        115                 120                 125

Val Glu Thr Asn Ser Tyr Asp Val Gln Arg Leu Leu His Val Lys Gly
    130                 135                 140

Lys Arg Asn Val Val Ala Gly Glu Val Glu Met Ser Trp Lys Ser Phe
145                 150                 155                 160

Asn Arg Gly Asp Val Phe Leu Leu Asp Leu Gly Lys Leu Ile Ile Gln
                165                 170                 175

Trp Asn Gly Pro Glu Ser Thr Arg Met Glu Arg Leu Arg Gly Met Thr
            180                 185                 190

Leu Ala Lys Glu Ile Arg Asp Gln Glu Arg Gly Gly Arg Thr Tyr Val
        195                 200                 205

Gly Val Val Asp Gly Glu Asn Glu Leu Ala Ser Pro Lys Leu Met Glu
    210                 215                 220

Val Met Asn His Val Leu Gly Lys Arg Arg Glu Leu Lys Ala Ala Val
225                 230                 235                 240

Pro Asp Thr Val Val Glu Pro Ala Leu Lys Ala Ala Leu Lys Leu Tyr
                245                 250                 255

His Val Ser Asp Ser Glu Gly Asn Leu Val Val Arg Glu Val Ala Thr
            260                 265                 270

Arg Pro Leu Thr Gln Asp Leu Leu Ser His Glu Asp Cys Tyr Ile Leu
        275                 280                 285

Asp Gln Gly Gly Leu Lys Ile Tyr Val Trp Lys Gly Lys Lys Ala Asn
    290                 295                 300

Glu Gln Glu Lys Lys Gly Ala Met Ser His Ala Leu Asn Phe Ile Lys
305                 310                 315                 320

Ala Lys Gln Tyr Pro Pro Ser Thr Gln Val Glu Val Gln Asn Asp Gly
                325                 330                 335

Ala Glu Ser Ala Val Phe Gln Gln Leu Phe Gln Lys Trp Thr Ala Ser
            340                 345                 350

Asn Arg Thr Ser Gly Leu Gly Lys Thr His Thr Val Gly Ser Val Ala
        355                 360                 365

Lys Val Glu Gln Val Lys Phe Asp Ala Thr Ser Met His Val Lys Pro
370                 375                 380

Gln Val Ala Ala Gln Gln Lys Met Val Asp Asp Gly Ser Gly Glu Val
385                 390                 395                 400

Gln Val Trp Arg Ile Glu Asn Leu Glu Leu Val Pro Val Asp Ser Lys
                405                 410                 415

Trp Leu Gly His Phe Tyr Gly Gly Asp Cys Tyr Leu Leu Tyr Thr
            420                 425                 430

Tyr Leu Ile Gly Glu Lys Gln His Tyr Leu Leu Tyr Val Trp Gln Gly
        435                 440                 445

Ser Gln Ala Ser Gln Asp Glu Ile Thr Ala Ser Ala Tyr Gln Ala Val
    450                 455                 460

Ile Leu Asp Gln Lys Tyr Asn Gly Glu Pro Val Gln Ile Arg Val Pro
465                 470                 475                 480
```

```
Met Gly Lys Glu Pro Pro His Leu Met Ser Ile Phe Lys Gly Arg Met
            485                 490                 495
Val Val Tyr Gln Gly Gly Thr Ser Arg Thr Asn Asn Leu Glu Thr Gly
            500                 505                 510
Pro Ser Thr Arg Leu Phe Gln Val Gln Gly Thr Gly Ala Asn Asn Thr
            515                 520                 525
Lys Ala Phe Glu Val Pro Ala Arg Ala Asn Phe Leu Asn Ser Asn Asp
530                 535                 540
Val Phe Val Leu Lys Thr Gln Ser Cys Cys Tyr Leu Trp Cys Gly Lys
545                 550                 555                 560
Gly Cys Ser Gly Asp Glu Arg Glu Met Ala Lys Met Val Ala Asp Thr
            565                 570                 575
Ile Ser Arg Thr Glu Lys Gln Val Val Glu Gly Gln Glu Pro Ala
            580                 585                 590
Asn Phe Trp Met Ala Leu Gly Gly Lys Ala Pro Tyr Ala Asn Thr Lys
            595                 600                 605
Arg Leu Gln Glu Glu Asn Leu Val Ile Thr Pro Arg Leu Phe Glu Cys
            610                 615                 620
Ser Asn Lys Thr Gly Arg Phe Leu Ala Thr Glu Ile Pro Asp Phe Asn
625                 630                 635                 640
Gln Asp Asp Leu Glu Glu Asp Val Phe Leu Leu Asp Val Trp Asp
            645                 650                 655
Gln Val Phe Phe Trp Ile Gly Lys His Ala Asn Glu Glu Lys Lys
            660                 665                 670
Ala Ala Ala Thr Thr Ala Gln Glu Tyr Leu Lys Thr His Pro Ser Gly
            675                 680                 685
Arg Asp Pro Glu Thr Pro Ile Ile Val Val Lys Gln Gly His Glu Pro
690                 695                 700
Pro Thr Phe Thr Gly Trp Phe Leu Ala Trp Asp Pro Phe Lys Trp Ser
705                 710                 715                 720
Asn Thr Lys Ser Tyr Glu Asp Leu Lys Ala Glu Ser Gly Asn Leu Arg
            725                 730                 735
Asp Trp Ser Gln Ile Thr Ala Glu Val Thr Ser Pro Lys Val Asp Val
            740                 745                 750
Phe Asn Ala Asn Ser Asn Leu Ser Ser Gly Pro Leu Pro Ile Phe Pro
            755                 760                 765
Leu Glu Gln Leu Val Asn Lys Pro Val Glu Leu Pro Glu Gly Val
770                 775                 780
Asp Pro Ser Arg Lys Glu Glu His Leu Ser Ile Glu Asp Phe Thr Gln
785                 790                 795                 800
Ala Phe Gly Met Thr Pro Ala Ala Phe Ser Ala Leu Pro Arg Trp Lys
            805                 810                 815
Gln Gln Asn Leu Lys Lys Glu Lys Gly Leu Phe
            820                 825
```

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:12:

GATGCGGATC CAAYGAYYTN ACNGCNCA                                            28

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:13:

GATGCATCGA TACRTGNGCN ACYTTYTC                                            28

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:14:

CTCGAGGGTG GCGACGACTC C                                                   21

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:15:

GCGGCCGCTT GACACCAGAC CAA                                                 23

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:16:

CAGCTATGAC CATGATTACG CCAA                                                24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

```
    (xi) SEQUENCE DESCRIPTION: SEQ ID NO:17:

ACGACGGCCA GTGAATTGCG TAAT                                          24

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Lys Val Ala Lys Val Glu Gln Val Lys Phe Asp Ala
1               5                   10
```